US007282608B2

(12) United States Patent
Raeppel et al.

(10) Patent No.: US 7,282,608 B2
(45) Date of Patent: *Oct. 16, 2007

(54) INHIBITORS OF HISTONE DEACETYLASE

(75) Inventors: Stephane Raeppel, St. Lazare (CA); Frederic Gaudette, Verdun (CA); Daniel Delorme, St-Lazare (CA)

(73) Assignee: Methylgene, Inc., St-Laurent, QC (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/531,406

(22) PCT Filed: Oct. 16, 2003

(86) PCT No.: PCT/CA03/01557

§ 371 (c)(1),
(2), (4) Date: Apr. 14, 2005

(87) PCT Pub. No.: WO2004/035525

PCT Pub. Date: Apr. 29, 2004

(65) Prior Publication Data

US 2006/0020131 A1 Jan. 26, 2006

Related U.S. Application Data

(60) Provisional application No. 60/419,688, filed on Oct. 17, 2002.

(51) Int. Cl.
C07C 233/65 (2006.01)
C07D 307/89 (2006.01)
C07D 277/82 (2006.01)
C07D 241/04 (2006.01)
C07D 213/56 (2006.01)

(52) U.S. Cl. .................. 564/164; 564/92; 549/434; 548/161; 548/263.8; 548/469; 546/337; 544/297; 544/360; 544/400

(58) Field of Classification Search .......... 548/161, 548/263.8, 469; 549/439, 434; 544/297, 544/360, 400; 546/337; 564/92, 164
See application file for complete search history.

(56) References Cited

U.S. PATENT DOCUMENTS

| 5,366,878 A | 11/1994 | Pederson et al. |
| 5,635,377 A | 6/1997 | Pederson et al. |
| 5,652,355 A | 7/1997 | Metelev et al. |
| 6,174,905 B1 | 1/2001 | Suzuki et al. |

FOREIGN PATENT DOCUMENTS

| EP | 0 847 992 A1 | 6/1998 |
| JP | 258863/96 | 9/1996 |
| WO | WO 01/38322 A1 | 5/2001 |
| WO | WO 01/70675 A2 | 9/2001 |

OTHER PUBLICATIONS

Weidle, U. H.; Grossmann, A., "XP-001098720—Inhibition of Histone Deacetylases: a New Strategy to Target Epigenetic Modifications for Anticancer Treatment", *Anticancer Research 20*, 2000, pp. 1471-1486.
Csordas, Adam., "On the Biological Role of Histone Acetylation," *Biochem. J.*, vol. 265 (1990) pp. 23-38.
Taunton, Jack, et al., "A Mammalian Histone Deacetylase Related to the Yeast Transcriptional Regulator Rpd3p," *Science*, vol. 272 (1996) pp. 408-411.
Grozinger, Christina M., et al., "Three Proteins Define a Class of Human Histone Deacetylases Related to Yeast Hdalp," *PNAS*, vol. 96 (1999) pp. 4868-4873.
Kao, Hung-Ying, et al., "Isolation of a Novel Histone Deacetylase Reveals that Class I and Class II Deacetylases Promote SMRT-Mediated Repression," *Genes & Development*, vol. 14 (2000) pp. 55-66.
Van den Wyngaert, Ilse, et al. "Cloning and Characterization of Human Histone Deacetylase 8," *FEBS Letters*, vol. 478 (2000) pp. 77-83.
Richon, Victoria M., et al. "A Class of Hybrid Polar Inducers of Transformed Cell Differentiation Inhibits Histone Deacetylases," *PNAS*, vol. 95 (1998) pp. 3003-3007.
Yoshida, Minoru & Beppu, Teruhiko, "Reversible Arrest of Proliferation of Rat 3Y1 Fibroblasts in Both the G1 and G2 Phases by Trichostatin A," *Experimental Cell Research*, vol. 177(1988) pp. 122-131.
Finnin, Michael S., et al., "Structures of a Histone Deacetylase Homologue Bound to the TSA and SAHA Inhibitors," *Nature*, vol. 401 (19999) pp. 188-193.
Yoshida, Minoru, et al., "Potent and Specific Inhibition of Mammalian Histone Deacetylase Both *In Vivo* and *In Vitro* by Trichostatin A," *J. Biol. Chem.*, vol. 265, No. 28 (1990) pp. 17174-17179.
Ramchandani, Shyam, et al., "Inhibition of Tumerigenesis by a Cytosine-DNA, Methyltransferase, Antisense Oligodeoxynucleotide,"*PNAS*, vol. 94 (1997) pp. 684-689.
Pon, Richard T., "Solid Phase Supports for Oligonucleotide Synthesis," *Methods in Molecular Biology*, vol. 20 (1993) pp. 465-496.
Meyer, Thomas, et al., "A Derivative of Staurosporine (CGP 41 251) Shows Selectivity for Protein Kinase C Inhibition and *In Vitro* Anti-Proliferative as Well as *In Vivo* Anti-Tumor Activity," *Int. J. Cancer*, vol. 43 (1989) pp. 851-856.

*Primary Examiner*—Shailendra Kumar
(74) *Attorney, Agent, or Firm*—McDonnell Boehnen Hulbert & Berghoff LLP

(57) ABSTRACT

The invention provides compoods and methods for treating cell proliferative-diseases. The invention provides new inhibitors of histone deacetylase enzymatic activity, compositions of the compounds comprising the inhibitors and a pharmaceutically acceptable carrier, excipient, or diluent, and methods of using the compounds to inhibit cellular proliferation in vitro and therapeutically.

6 Claims, 1 Drawing Sheet

INHIBITORS OF HISTONE DEACETYLASE

This application is a 371 of PCT/CA03/01557, filed Oct. 16, 2003, which claims benefit of 60/419,688, filed Oct. 17, 2002.

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23–38 (1990) teaches that histones are subject to posttranslational acetylation of the α,ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science*, 272: 408411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA*, 96: 4868–4873 (1999), teaches that HDACs is divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.*, 14: 55–66 (2000), discloses HDAC7, a new member of the second class of HDACs. Van den Wyngaert, *FEBS*, 478: 77–83 (2000) discloses HDAC8, a new member of the first class of HDACs.

Richon et al., *Proc. Natl. Acad. Sci. USA*, 95: 3003–3007 (1998), discloses that HDAC activity is inhibited by trichostatin A (TSA), a natural product isolated from *Streptomyces hygroscopius*, and by a synthetic compound, suberoylanilide hydroxamic acid (SAHA). Yoshida and Beppu, *Exper. Cell Res.*, 177: 122–131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188–193 (1999), teaches that TSA and SAHA inhibit cell growth, induce terminal differentiation, and prevent the formation of tumors in mice. Suzuki et al., U.S. Pat. No. 6,174,905, EP 0847992, JP 258863/96, and Japanese Application No. 10138957, disclose benzamide derivatives that induce cell differentiation and inhibit HDAC. Delorme et al., WO 01/38322 and PCT IB01/00683, disclose additional compounds that serve as HDAC inhibitors.

These findings suggest that inhibition of HDAC activity represents a novel approach for intervening in cell cycle regulation and that HDAC inhibitors have great therapeutic potential in the treatment of cell proliferative diseases or conditions. To date, few inhibitors of histone deacetylase are known in the art. There is thus a need to identify additional HDAC inhibitors and to identify the structural features required for potent HDAC inhibitory activity.

BRIEF SUMMARY OF THE INVENTION

The invention provides compounds and methods for treating cell proliferative diseases. The invention provides new inhibitors of histone deacetylase enzymatic activity.

In a first aspect, the invention provides compounds that are useful as inhibitors of histone deacetylase.

In a second aspect, the invention provides a pharmaceutical composition comprising an inhibitor of histone deacetylase according to the invention and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase of the invention.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

Figure 1:
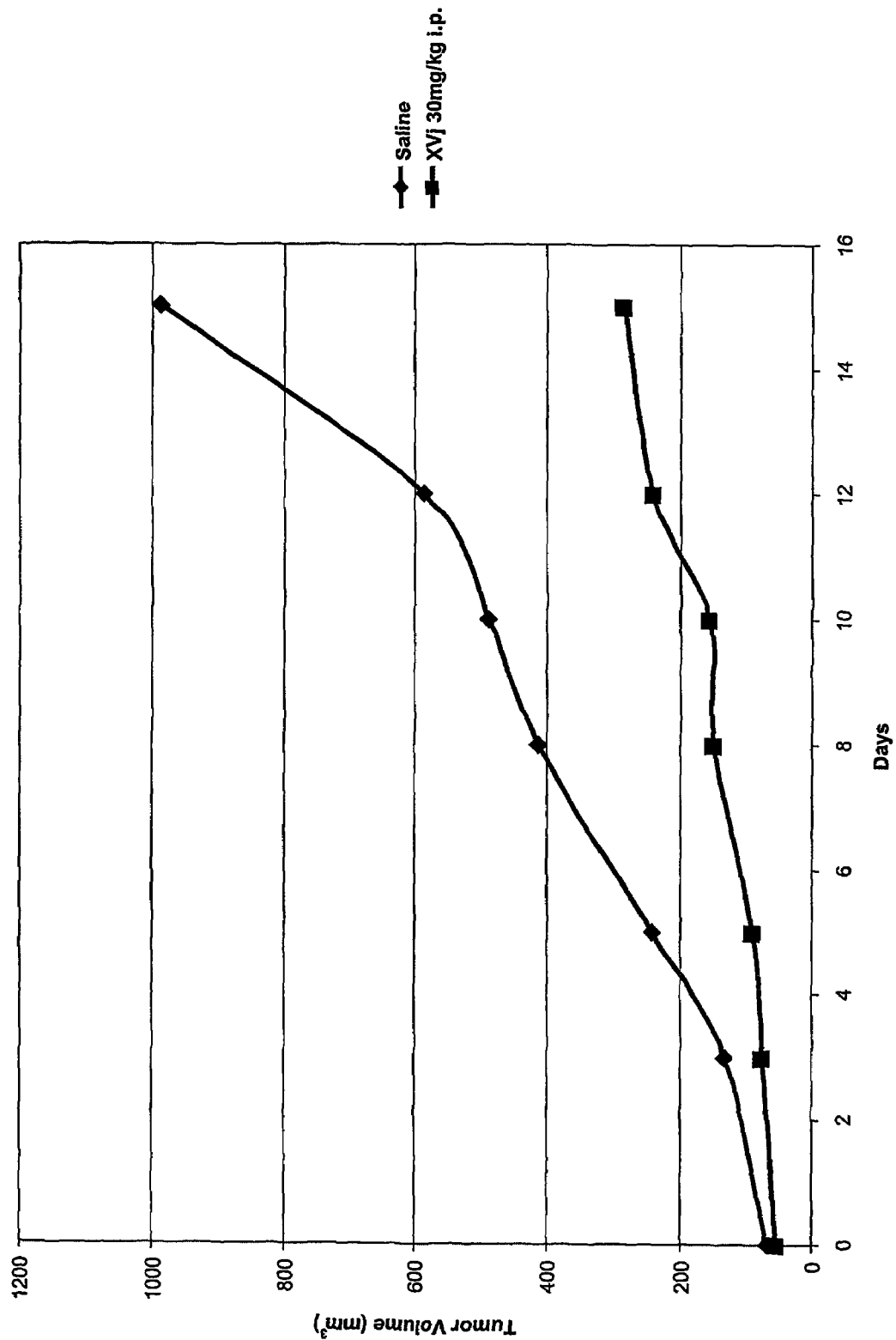
FIG. 1 displays antineoplastic effects of a histone deacetylase inhibitor according to the invention on human tumor xenografts in vivo, as described in Example 51, infra.

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

In one embodiment of the first aspect, the invention comprises compounds of the following formula:

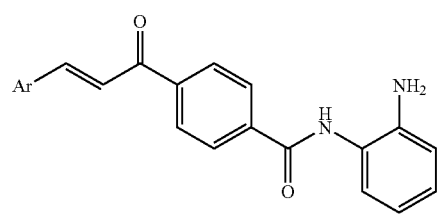

and pharmaceutically acceptable salts thereof, wherein

Ar is aryl or heteroaryl, each of which is optionally substituted with from 1 to 3 substituents.

Preferably, Ar is aryl or pyridinyl in the compound of paragraph [0014].

Preferred substituents of Ar include halo, $C_1$–$C_6$-hydrocarbyl optionally substituted with halo, $C_1$–$C_6$-hydrocarbyloxy optionally substituted with halo. Particularly preferred substituents include fluoro, chloro, methoxy, cyclopropyloxy, and cyclopentyloxy.

In a preferred embodiment of the compound according to paragraph [0014], Ar is selected from the following:

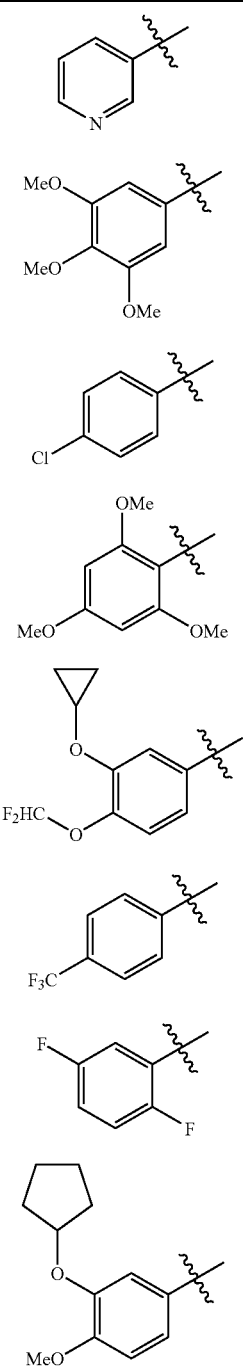

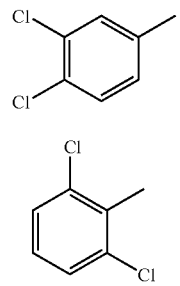

Preferred compounds of paragraph [0014] include those of Table 6 below.

In another embodiment of the first aspect, the invention comprises compounds of the following formula:

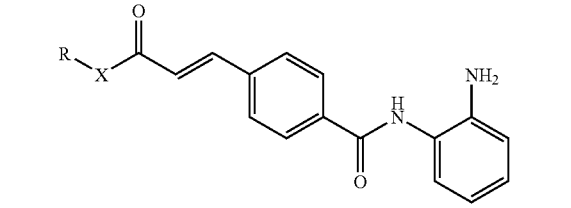

and pharmaceutically acceptable salts thereof, wherein

X is —N($R^1$)—, —O—, or —S—; or X is a nitrogen-containing heterocyclyl in which a nitrogen is covalently bound to the adjacent carbonyl in structure V and is optionally substituted with from 1 to 3 substituents; and R and $R^1$ independently are —H, or optionally substituted a) $C_1$–$C_6$-hydrocarbyl or b) $R^2$-L-, wherein $R^2$ is aryl or heteroaryl, L is $C_0$–$C_6$-hydrocarbyl-$L^1$-$C_0$–$C_6$-hydrocarbyl, and $L^1$ is a covalent bond, —O—, —S—, or —NH—.

Preferably in the compound according to paragraph [0019], X is —NH—, —O—, morphilin-4-yl, piperidin-1-yl, piperizin-1-yl, or pyrrolidin-1-yl.

In another preferred embodiment of the compound according to paragraph [0019], X is —N($R^1$)— wherein $R^1$ is optionally substituted methyl or ethyl. Preferably $R^1$ is cyanoethyl or pyridinylmethyl.

Preferably in the compound according to paragraph [0019], R is $R^2$-L- wherein $R^2$ is phenyl, pyridinyl, indyl, or indolyl and L is a covalent bond, methyl, ethyl, or oxyethyl.

Preferred subsbtuents of R include methoxy and hydroxy.

In a preferred embodiment of the compound according to paragraph [0019], the combination of R—X— is selected from the following:

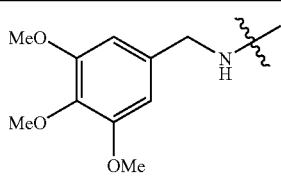

-continued

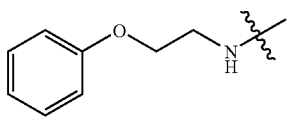

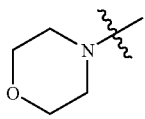

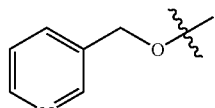

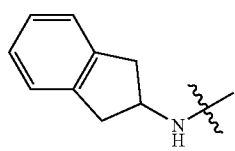

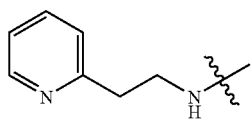

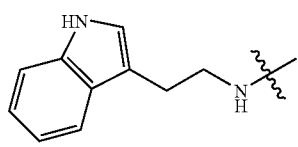

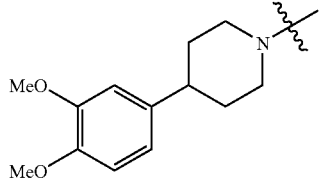

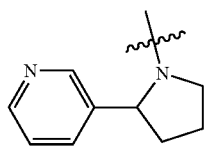

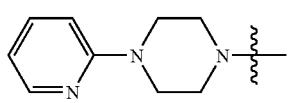

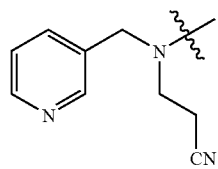

-continued

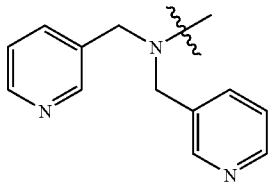

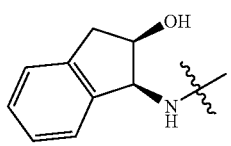

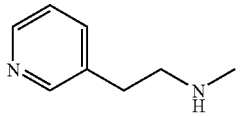

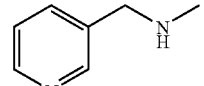

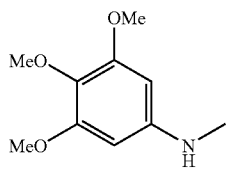

Preferred compounds according to paragraph [0019] include those listed in Table 7.

In another embodiment of the first aspect, the invention comprises compounds of the following formula:

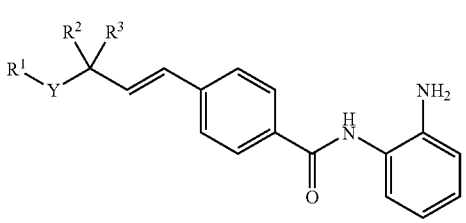

and pharmaceutically acceptable salts thereof, wherein

Y is —N($R^4$)—, —O—, —S—, —N($R^4$)$SO_2$—, —$SO_2$—N($R^4$)—, —$SO_2$—, —N($R^4$)—C(O)—, —C(O)—N($R^4$)—, —NHC(O)NH—, —N($R^4$)C(O)O—, —OC(O)N($R^4$)—, or a covalent bond, and $R^1$, $R^2$, and $R^3$ independently are —H or $R^a$—$C_0$-$C_6$-hydrocarbyl wherein $R^a$ is —H or $R^a$ is aryl or heteroaryl, each of which is optionally substituted with from 1 to 3 substituents.

$R^4$ is —H, —C(O)—$R^b$, —C(O)O—$R^b$, —C(O)NH—$R^b$, or $R^c$—$C_0$-$C_6$-hydrocarbyl wherein $R^b$ is —H or —$C_1$-$C_6$-hydrocarbyl, and $R^c$ is —H, or aryl or heteroaryl each of which is optionally substituted with from 1 to 3 substituents.

In the compound of paragraph [0026], $R^2$ and $R^3$ are preferably both —H.

In the compound of paragraph [0026], Y is preferably —NH—, —SO$_2$NH—, or —N(R$^4$)— wherein R$^4$ is —C(O)O—C$_1$–C$_6$-hydrocarbyl.

In the compound of paragraph [0026], R$^1$ is preferably aryl, benzothiazolyl, pyrimidinyl, triazolyl, benzodioxolenyl, or pyridinyl.

Preferred substituents of R$^1$ include C$_1$–C$_6$-hydrocarbyl, C$_1$–C$_6$-hydrocarbyloxy (e.g., methoxy and cyclopropyloxy) halo, methylthio, and acetyl.

In a preferred embodiment of the compound according to paragraph [0026], R$^1$—Y— is selected from the following:

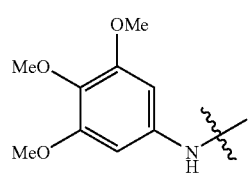
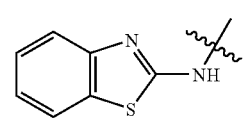
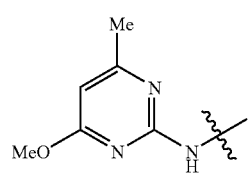
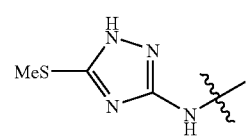
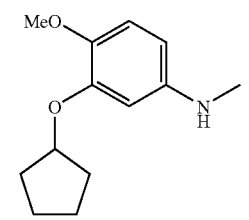
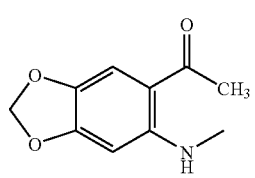
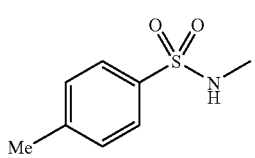

-continued

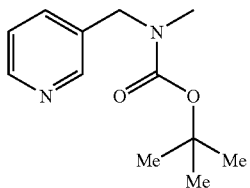
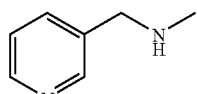
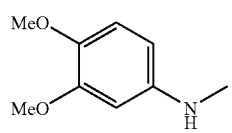
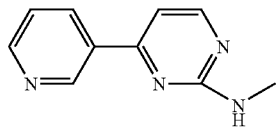
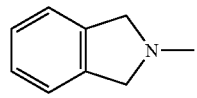
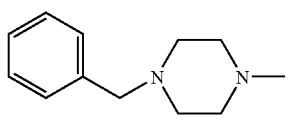
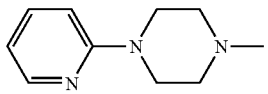
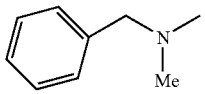
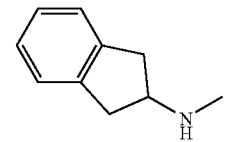

Preferred compounds according to paragraph [0026] include those listed in Table 8.

In another embodiment of the first aspect, the invention comprises compounds of formula:

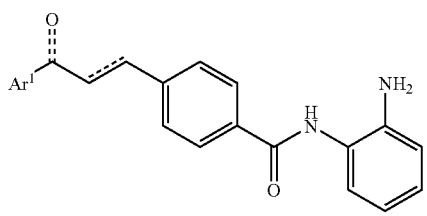

and pharmaceutically acceptable salts thereof, wherein $Ar^1$ is aryl or heteroaryl optionally substituted with from 1–3 substituents independently selected from —$NO_2$, $CH_3O$—, and morpholinyl (e.g., morpholin-4-yl).

In a preferred embodiment of the compound according to paragraph [0033], $Ar^1$ is aryl (e.g., phenyl).

In preferred embodiments of the compound according to paragraph [0033], $Ar^1$ is selected from:

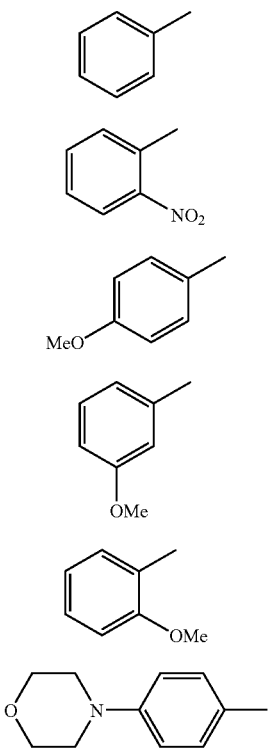

Preferred compounds according to paragraph [0033] included those listed in Table 9.

In the second aspect, the invention comprises a composition comprising a compound according to one of paragraphs [0014]–[0036] and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase according to one of paragraphs [0014]–[0037].

In another aspect, the invention comprises treating a mammal (preferably a human) suffering from a cell proliferative diseases or conditions a therapeutically effective amount of a composition according to paragraph [0037].

For purposes of the present invention, the following definitions will be used (unless expressly stated otherwise):

As used herein, the terms "histone deacetylase" and "HDAC" are intended to refer to any one of a family of enzymes that remove acetyl groups from the, -amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, and HDAC-8. In some other preferred embodiments, the histone deacetylase is derived from a protozoal or fungal source.

The terms "histone deacetylase inhibitor" and "inhibitor of histone deacetylase" are used to identify a compound having a structure as defined herein, which is capable of interacting with a histone deacetylase and inhibiting its enzymatic activity. "Inhibiting histone deacetylase enzymatic activity" means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed herein exist in multiple tautomeric forms, all of which are intended to be encompassed by any given tautomeric structure.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$–$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1–8 carbon atoms, and more preferably 1–6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$–$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2–8 carbon atoms, and more preferably 2–6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2–8 carbon atoms, and more preferably 2–6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propenylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

An "aryl" group is a $C_6$–$C_{14}$ aromatic moiety comprising one to three aromatic rings, which is optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$–$C_6$)alk($C_6$–$C_{10}$)aryl, including, without limitation, benzyl, phenethyl, and naphthylmethyl.

A "heterocyclyl" or "heterocyclic" group is a ring structure having from about 3 to about 12 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having an annular O and/or S atom adjacent to another annular O or S.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. The term "heteroaryl" is also meant to encompass monocyclic and bicyclic groups. For example, a heteroaryl group may be pyrimidinyl, pyridinyl, benzimidazolyl, thienyl, benzothiazolyl, benzofuranyl and indolinyl. A "heteroarylalkyl" or "heteroarylalkyl" group comprises a heteroaryl group covalently linked to an alkyl group, either of which is independently optionally substituted or unsubstituted. Preferred heteroalkyl groups comprise a $C_1$–$C_6$ alkyl group and a heteroaryl group having 5, 6, 9, or 10 ring atoms. Specifically excluded from the scope of this term are compounds having adjacent annular O and/or S atoms. Examples of preferred heteroarylalkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:
(a) halo, cyano, oxo, carboxy, formyl, nitro, amino, amidino, guanidino,
(b) $C_1$–$C_5$ alkyl or alkenyl or arylalkyl imino, carbamoyl, azido, carboxamido, mercapto, hydroxy, hydroxyalkyl, alkylaryl, arylalkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, $C_2$–$C_8$ acyl, $C_2$–$C_8$ acylamino, $C_1$–$C_8$ alkylthio, arylalkylthio, arylthio, $C_1$–$C_8$ alkylsulfinyl, arylalkylsulfinyl, arylsulfinyl, $C_1$–$C_8$ alkylsulfonyl, arylalkylsulfonyl, arylsulfonyl, $C_0$–$C_6$ N-alkyl carbamoyl, $C_2$–$C_{15}$ N,N-dialkylcarbamoyl, $C_3$–$C_7$ cycloalkyl, aroyl, aryloxy, arylalkyl ether, aryl, aryl fused to a cycloalkyl or heterocycle or another aryl ring, $C_3$–$C_7$ heterocycle, or any of these rings fused or spiro-fused to a cycloalkyl, heterocyclyl, or aryl, wherein each of the foregoing is further optionally substituted with one more moieties listed in (a), above; and
(c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$–$C_8$ hydroxyalkyl, $C_1$–$C_3$ alkylaryl, aryl-$C_1$–$C_3$ alkyl, $C_1$–$C_8$ alkyl, $C_1$–$C_8$ alkenyl, $C_1$–$C_8$ alkoxy, $C_1$–$C_8$ alkoxycarbonyl, aryloxycarbonyl, aryl-$C_1$–$C_3$ alkoxycarbonyl, $C_2$–$C_8$ acyl, $C_1$–$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5–6 membered mono- and 9–14 membered bi-cyclic moieties fused to the parent cyclic moiety to form a bi- or tricyclic fused ring system. For example, an optionally substituted phenyl includes the following:

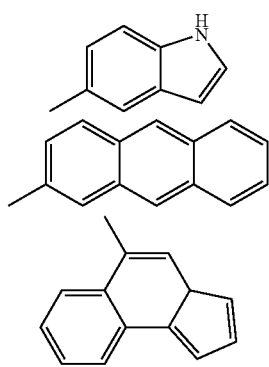

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-fluorophenyl, 3,4-dichlorophenyl, 3chloro-4-fluoro-phenyl, 2-fluor-3-propylphenyl. As another non-limiting example, substituted n-octyls include 2,4 dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Preferred embodiments of the invention also include combinations of the preferred embodiments expressly described herein.

Synthesis

Compounds of general formula I were prepared according to the synthetic routes depicted in Schemes 1 and 2. In some embodiments, 4-acetylbenzoic acid was reacted with an aromatic and/or heteroaromatic aldehyde in a solvent such as methanol (MeOH) in the presence of an aqueous solution of sodium hydroxide (1N) to give after filtration or acidification until pH=5–6 and filtration, the chalcone II. Compound II was first treated with the coupling reagent benzotriazol-1-yloxy-tris(dimethylamino)phosphonium hexafluorophosphate (BOP reagent) in a solvent such as N,N-dimethylformamide (DMF) in the presence of triethylamine ($Et_3N$). The resulting activated ester intermediate formed in situ was finally reacted with 1,2-phenylenediamine to afford the compound I (Scheme 1).

Scheme 1

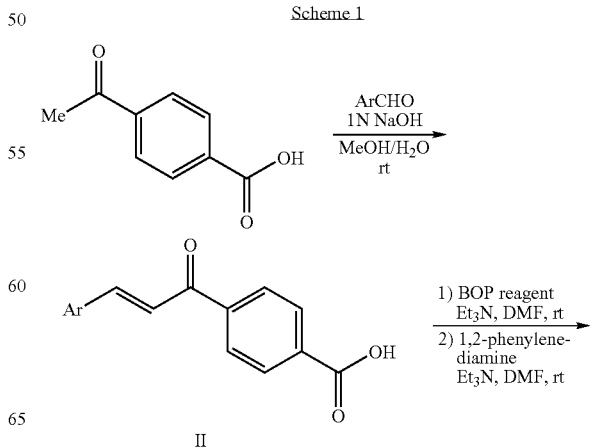

-continued

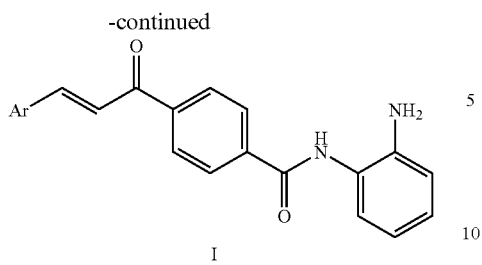

I

Alternatively, in some other embodiments, 4-acetylbenzoic acid was first treated with the coupling reagent benzotriazol-1-yloxy-tris(dimethylamino)phosphonium hexafluorophosphate in a solvent such as N,N-dimethylformamide in the presence of triethylamine. The resulting activated ester intermediate formed in situ was then reacted with t-butyl (2-amino-phenyl)-carbamate to afford the common acetophenone derivative III. Chalcone IV was prepared by the Claisen-Schmidt condensation of compound III with an appropriate aromatic and/or heteroaromatic aldehyde in a solvent such as methanol in the presence of an aqueous solution of sodium hydroxide (1N). N-Boc protective group of aniline IV was finally cleaved by a wet solution of trifluoroacetic acid (TFA 95% in water) in a solvent such as dichloromethane ($CH_2Cl_2$) to furnish the compound I (Scheme 2).

Scheme 2

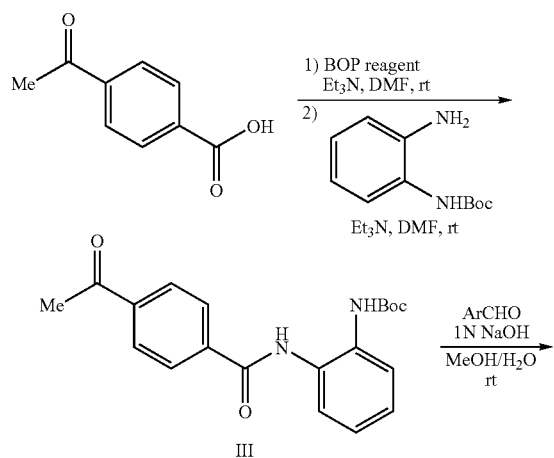

-continued

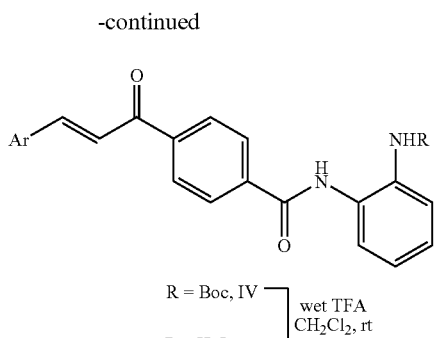

Compounds of general formula V were prepared according to the synthetic routes depicted in Scheme 3 and 4. In certain preferred embodiments, methyl 4-formylbenzoate was converted into the pure trans-α,β-unsaturated ester VI by reaction with the anion of t-butyl acetate in a mixture of solvent such as tetrahydrofuran (THF) and hexane followed by the treatment with 2-chloro-4,6-dimethoxy-1,3,5-triazine as a new dehydrating agent. Acidic hydrolysis of t-butyl ester VI was performed by a wet solution of trifluoroacetic acid (95% in water) in a solvent such as dichloromethane to give the compound VII. The formation of compounds IX was carried out by two complementary methods depending of the nucleophilicity of RXH. In the method A, the carboxylic acid VII was first converted into the stable activated ester VIII by using the coupling reagent benzotriazol-1-yloxy-tris(dimethylamino)phosphonium hexafluorophosphate (BOP reagent) in a solvent such as N,N-dimethylformamide in the presence of triethylamine. This stable activated ester VIII was then reacted with a weak nucleophile (e.g., RXH=anilines or aminoheteroaryls) in a solvent such as dichloromethane in the presence of triethylamine to afford the compound IX. In the method B, the same activated ester VIII intermediate formed in situ from the carboxylic acid VII, was then reacted with a strong nucleophile (e.g., RXH=amines, alcohols, thiols, hydroxylamine and derivatives, or hydrazine and derivatives) in a solvent such as N,N-dimethylformamide in the presence of triethylamine to afford the compound IX.

Scheme 3

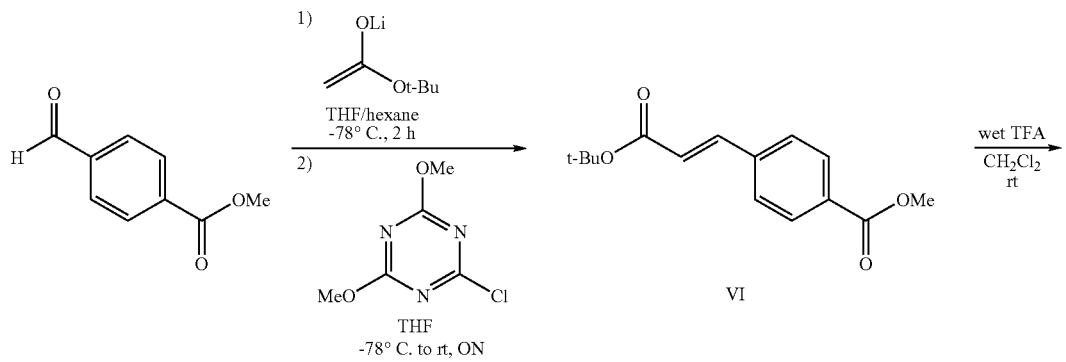

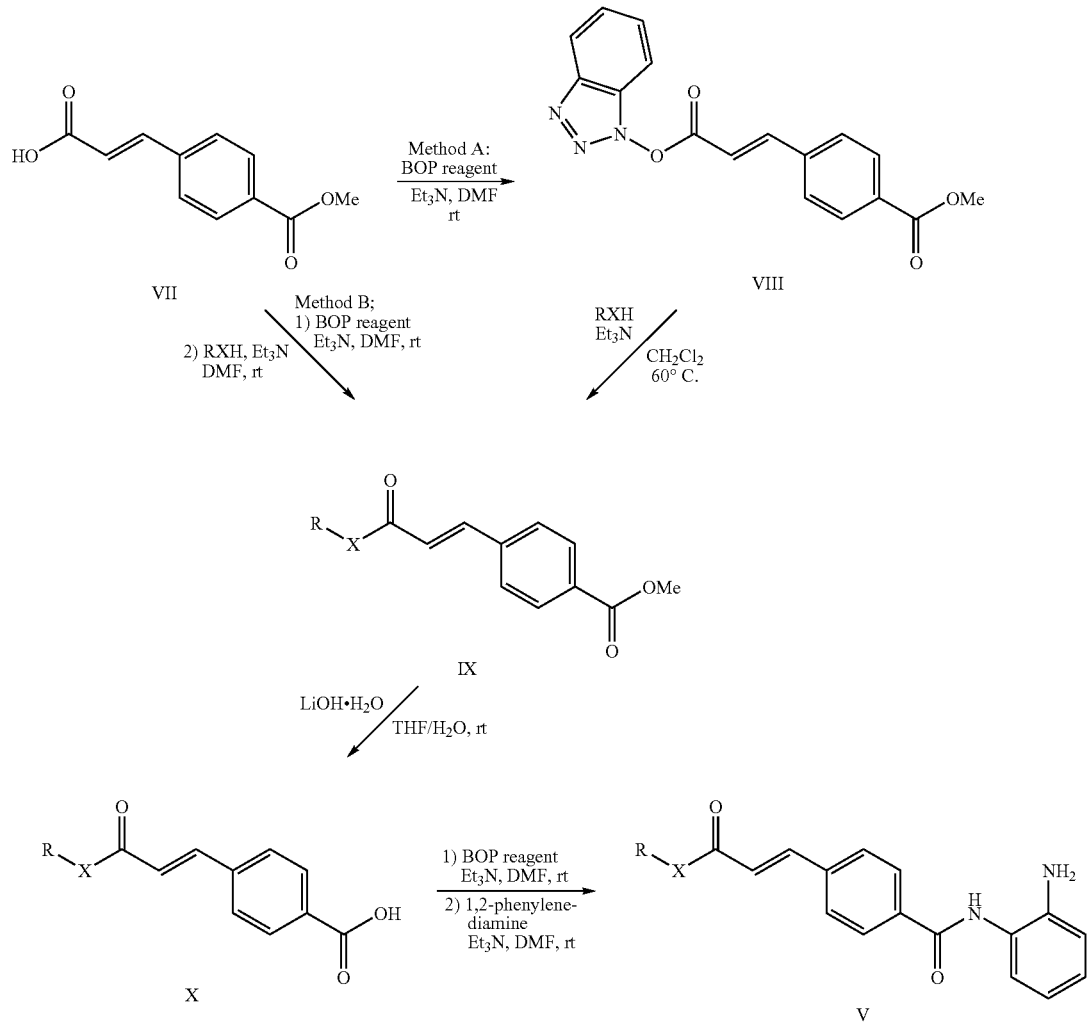

Basic hydrolysis of methyl ester IX was performed by a aqueous solution of lithium hydroxide in a solvent such as tetrahydrofuran to lead to the compound X. Carboxylic acid X was finally treated with the coupling reagent benzotriazol-1-yloxy-tris(dimethylamino)phosphonium hexafluorophosphate (BOP reagent) in a solvent such as N,N-dimethylformamide in the presence of triethylamine. The resulting activated ester intermediate formed in situ was then reacted with 1,2-phenylenediamine to afford the compound V (Scheme 3).

Alternatively, in some other embodiments, 4-carboxybenzaldehyde was first converted into the acid chloride intermediate by using thionyl chloride ($SOCl_2$) in a solvent such as dichloromethane in the presence of a catalytic amount of N,N-dimethylformamide. The resulting acid chloride intermediate was then reacted with t-butyl (2-amino-phenyl)-carbamate to afford the common benzaldehyde derivative XI.

Scheme 4

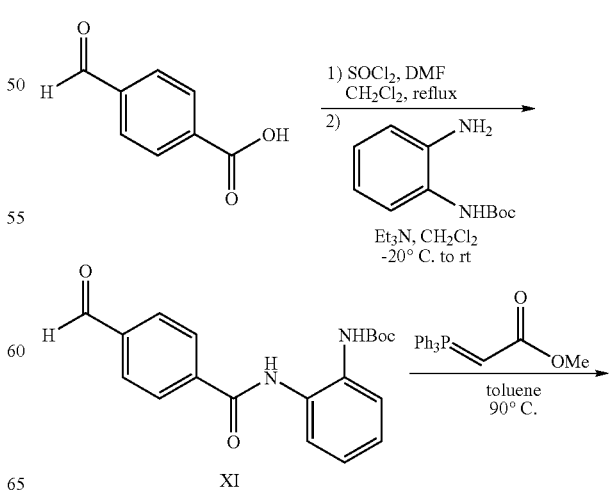

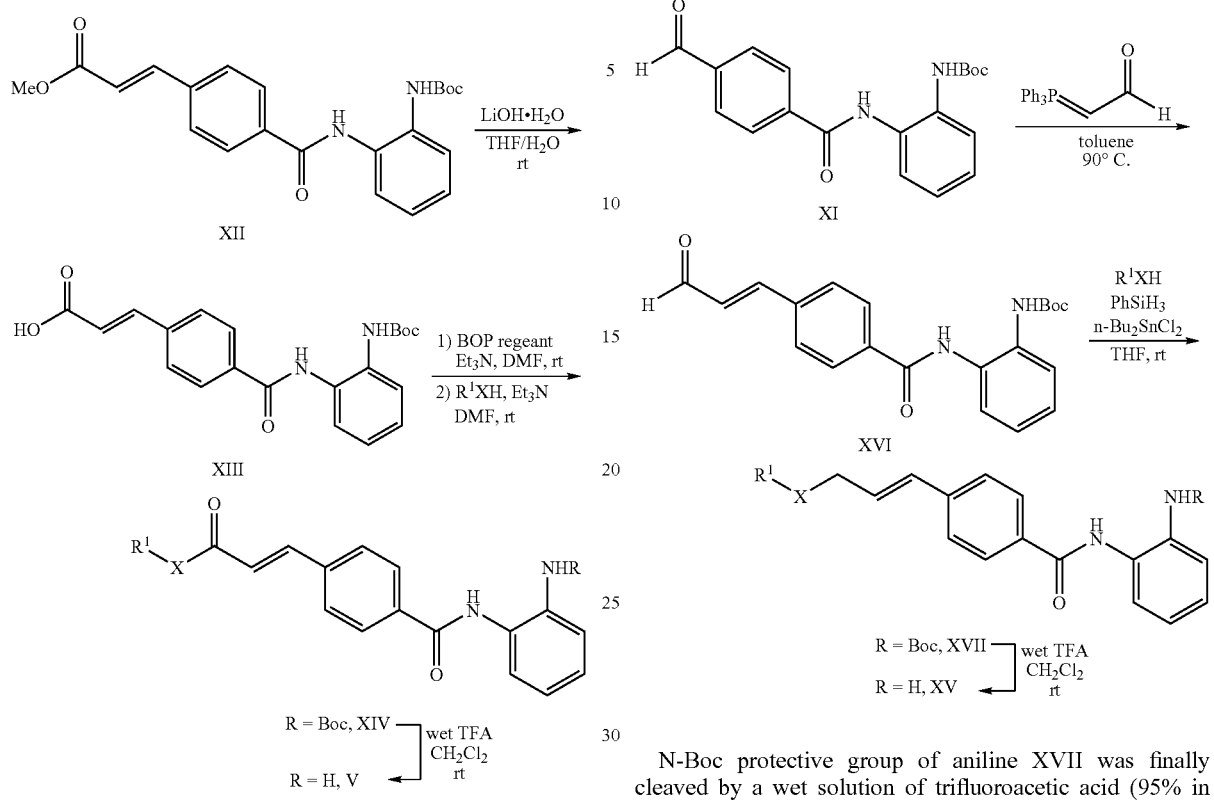

Wittig olifination of the aldehyde XI was performed with methyl (triphenyl-phosphoranylidene)acetate in a solvent such as toluene to provide the trans-α,β-unsaturated ester XII. Basic hydrolysis of methyl ester XII was performed by a aqueous solution of lithium hydroxide in a solvent such as tetrahydrofuran to lead to the compound XIII. Carboxylic acid XIII was treated with the coupling reagent benzotriazol-1-yloxy-tris(dimethylamino)phosphonium hexafluorophosphate (BOP reagent) in a solvent such as N,N-dimethylformamide in the presence of triethylamine. The resulting activated ester intermediate formed in situ was then reacted with the nucleophile $R^1XH$ to afford the compound XIV. N-Boc protective group of aniline XIV was finally cleaved by a wet solution of trifluoroacetic acid (95% in water) in a solvent such as dichloromethane to furnish the compound V (Scheme 4).

Compounds of general formula XV were prepared according to the synthetic routes depicted in Schemes 5–7. Thus, Wittig olifination of aldehyde XI was performed with the (triphenylphosphoranylidene)-acetaldehyde reagent in a solvent such as toluene to provide the trans-α,β-unsaturated aldehyde XVI. In certain preferred embodiments, the formation of compounds XVII was performed by a reductive amination following the described method depending of the nucleophilicity of $R^1XH$. Aldehyde XVI was first mixed with a weak nucleophile (e.g., $R^1XH$=anilines or aminoheteroaryls) in a solvent such as tetrahydrofuran in the presence of a catalytic amount of dibutyltin dichloride. The resulting iminium intermediate formed in situ was then reacted with the reductive reagent phenylsilane to afford the compound XVII.

N-Boc protective group of aniline XVII was finally cleaved by a wet solution of trifluoroacetic acid (95% in water) in a solvent such as dichloromethane to furnish the compound XV (Scheme 5).

Alternatively, in some other embodiments, the trans-α,β-unsaturated aldehyde XVI was reduced into the primary allylic alcohol XVIII by the reductive reagent sodium borohydride in a solvent such as ethanol. This alcohol XVIII was then reacted with a nucleophile $R^1XH$ according to a Mitsunobu type reaction in a solvent such as tetrahydrofuran in the presence of triphenylphosphine and diethyl azodicarboxylate (DEAD) to furnish the compound XVII. N-Boc protective group of aniline XVII was finally cleaved by a wet solution of trifluoroacetic acid (95% in water) in a solvent such as dichloromethane to furnish the compound XV (Scheme 6).

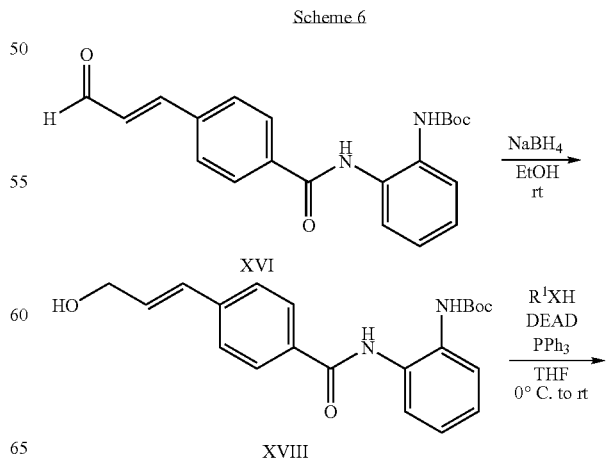

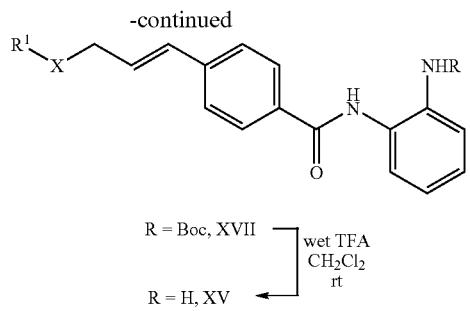

R = Boc, XVII
R = H, XV
wet TFA
CH$_2$Cl$_2$
rt

Moreover, in some other embodiments, Wittig olefination of methyl 4-formylbenzoate was performed using either the (triphenylphosphoranylidene)-acetaldehyde reagent in a solvent such as toluene or the (1,3-dioxolan-2-yl)methyltriphenylphosphonium bromide reagent in the presence of TDA-1 {tris[2-(2-methoxyethoxy)ethyl]amine) and potassium carbonate in a biphasic medium such as dichloromethane/water followed by an acidic hydrolysis to provide the trans-α,β-unsaturated aldehyde XIX. Aldehyde XIX was first mixed with a nucleophile (R$^1$R$^2$NH) in a solvent such as dichloromethane or 1,2-dichloroethane. The resulting iminium intermediate formed in situ was then reacted with the reductive reagent sodium triacetoxyborohydride [NaBH(OAc)$_3$] to afford the compound XX. In the pathway A, the basic hydrolysis of the methyl ester and protection of the secondary amine of compound XX (R$^1$=alkyl, R$^2$=H) were performed at the same time in the presence of an aqueous solution of sodium hydroxide (1N) and the protective reagent di-tert-butyl dicarbonate [(Boc)$_2$O] in a solvent such as 1,4-dioxane to lead to the compound XXI. Carboxylic acid XXI was first treated with the coupling reagent benzotriazol-1-yloxy-tris(dimethylamino)phosphonium hexafluorophosphate (BOP reagent) in a solvent such as N,N-dimethylformamide in the presence of triethylamine. The resulting activated ester intermediate formed in situ was then reacted with 1,2-phenylenediamine to afford the compound XXII. N-Boc protective group of amine XXII was finally cleaved by a solution of wet trifluoroacetic acid (95% in water) in a solvent such as dichloromethane to furnish the compound XV (Scheme 7).

Scheme 7

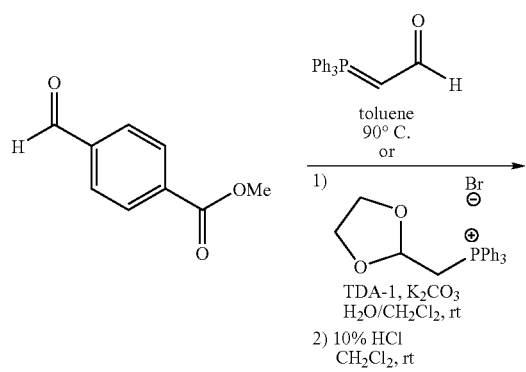

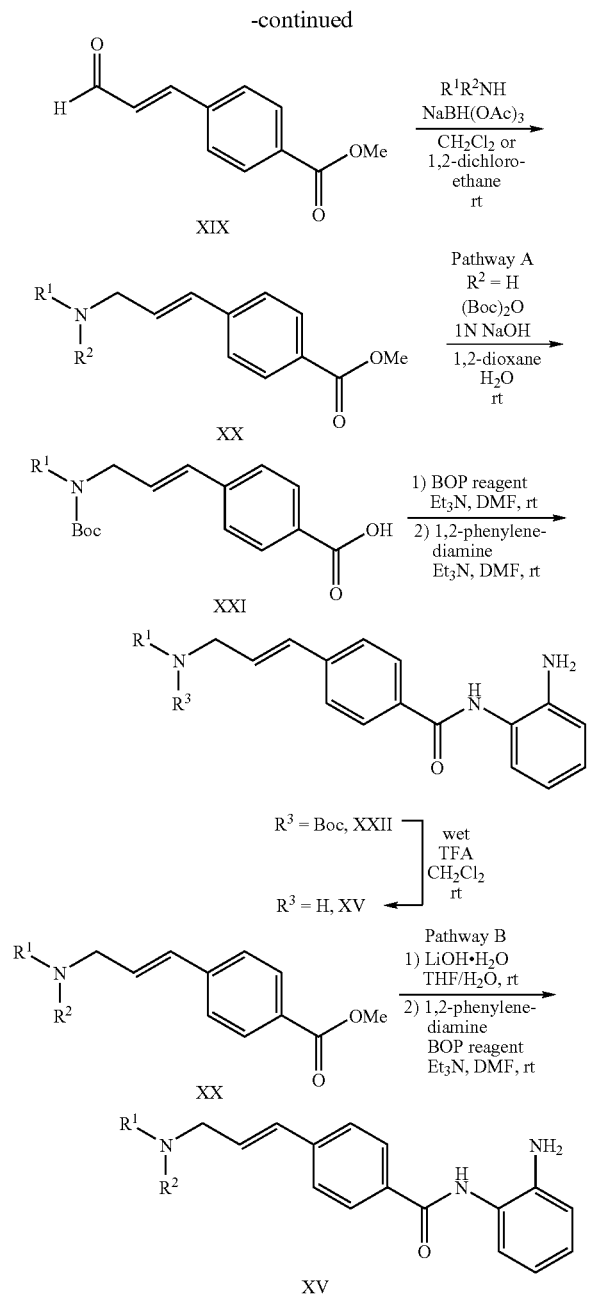

In the pathway B, the methyl ester XX was directly converted into the final compound XV after basic hydrolysis and coupling with 1,2-phenylenediamine (Scheme 7).

Compounds of general formula XXIV were prepared according to the synthetic routes depicted in Schemes 8 and 9. In some embodiments, 4-formylbenzoic acid was reacted with an aryl and/or heteroaryl methyl ketone in a solvent such as methanol (MeOH) in the presence of an aqueous solution of sodium hydroxide (1N) to give after filtration the chalcone XXIII. Compoud XXIII was first treated with the coupling reagent benzotriazol-1-yloxy-tris(dimethylamino) phosphonium hexafluorophosphate (BOP reagent) in a solvent such as N,N-dimethylformamide (DMF) in the presence of triethylamine (Et$_3$N). The resulting activated ester intermediate formed in situ was finally reacted with 1,2-phenylenediamine to afford the compound XXIV (Scheme 8).

in a solvent such as dichloromethane (CH$_2$Cl$_2$) to furnish the compound XXIV (Scheme 9).

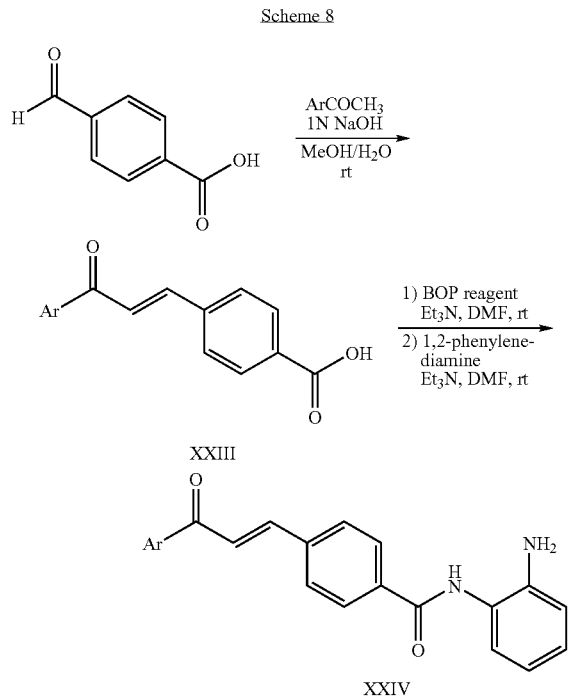

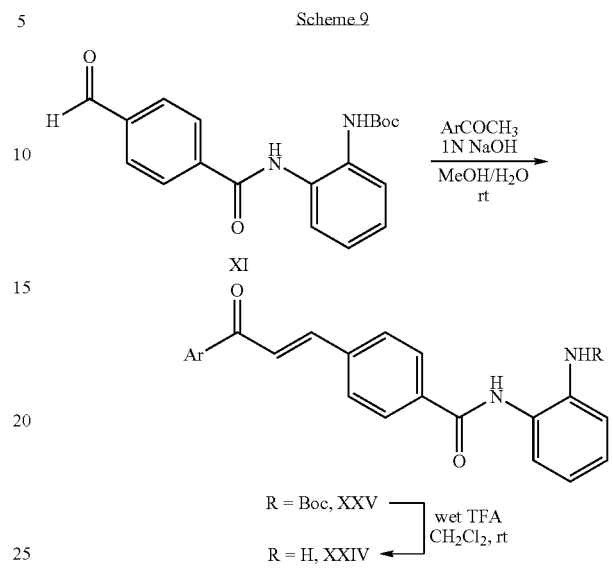

Alternatively, in some other embodiments, chalcone XXV was prepared by the Claisen-Schmidt condensation of benzaldehyde derivative XI with an appropriate aryl and/or heteroaryl methyl ketone in a solvent such as methanol in the presence of an aqueous solution of sodium hydroxide (1N). N-Boc protective group of aniline XXV was finally cleaved by a wet solution of trifluoroacetic acid (TFA 95% in water)

Compounds of general formula XXVII and XXIX were prepared according to the synthetic routes depicted in Scheme 10. Thus, selective reduction of the double bond of compound XXIII was carried out by using the reductive reagent benzenesulfonyl hydrazide in a solvent such as N,N-dimethylformamide to produce compound XXVI. Carboxylic acid XXVI was first treated with the coupling reagent benzotriazol-1-yloxy-tris(dimethylamino)phosphonium hexafluorophosphate (BOP reagent) in a solvent such as N,N-dimethylformamide in the presence of triethylamine. The resulting activated ester intermediate formed in situ was finally reacted with 1,2-phenylenediamine to afford the compound XXVII.

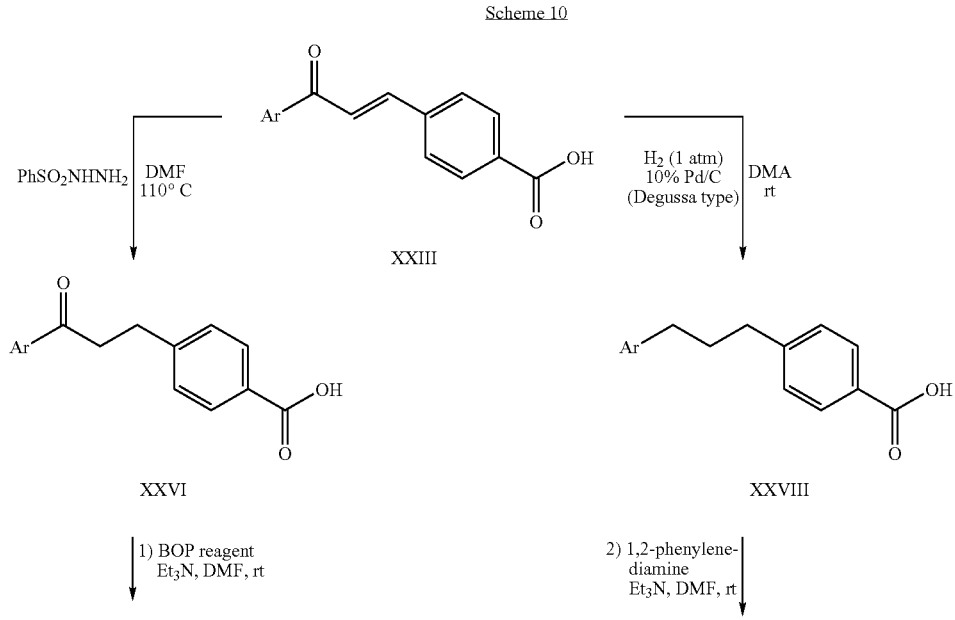

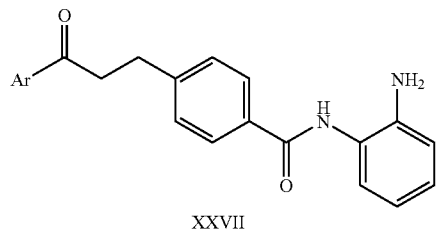

XXVII

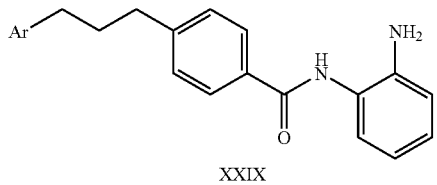

XXIX

Moreover, the complete reduction of the α,β-unsaturated ketone XXIII into the saturated compound XXVIII was performed by an hydrogenation catalyzed by 10% of palladium on charcoal (Degussa type) in a solvent such as N,N-dimethylacetamide (DMA). Then, the carboxylic acid XXVIII was first treated with the coupling reagent benzotriazol-1-yloxy-tris(dimethylamino)phosphonium hexafluorophosphate (BOP reagent) in a solvent such as N,N-dimethylformamide in the presence of triethylamine. The resulting activated ester intermediate formed in situ was finally reacted with 1,2-phenylenediamine to afford the compound XXIX (Scheme 10).

Compounds of general formula XXX were prepared according to the synthetic route depicted in Scheme 11. Thus, Sonogashira type reaction between methyl 4-bromobenzoate and (trimethylsilyl)acetylene was carried out by a catalytic amount of palladium catalyst and copper iodide in the presence of Et₃N in a solvent such THF to afford the protected alkyne XXXI. Basic deprotecton of TMS group of XXXI was performed by potassium carbonate in the presence of methanol to give the alkyne XXXII. Hydroboration of the triple bond of XXXII was performed by the catecholborane reagent in a solvent such THF followed by acidic hydrolysis of the boronate intermediate to furnish boronic acid XXXIII. Allylic amine XXXIV was elaborated according to the Petasis type reaction by reacting the vinyl-boronic acid XXXIII with a pre-formed mixture between an amino compound (R¹R²NH) and an aldehyde (R³CHO) in a solvent such 1,4-dioxane. Finally, the methyl ester XXIV was converted into the final compound XXX after basic hydrolysis and coupling with 1,2-phenylenediamine.

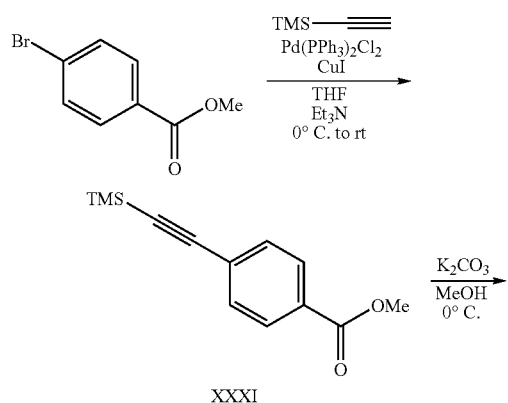

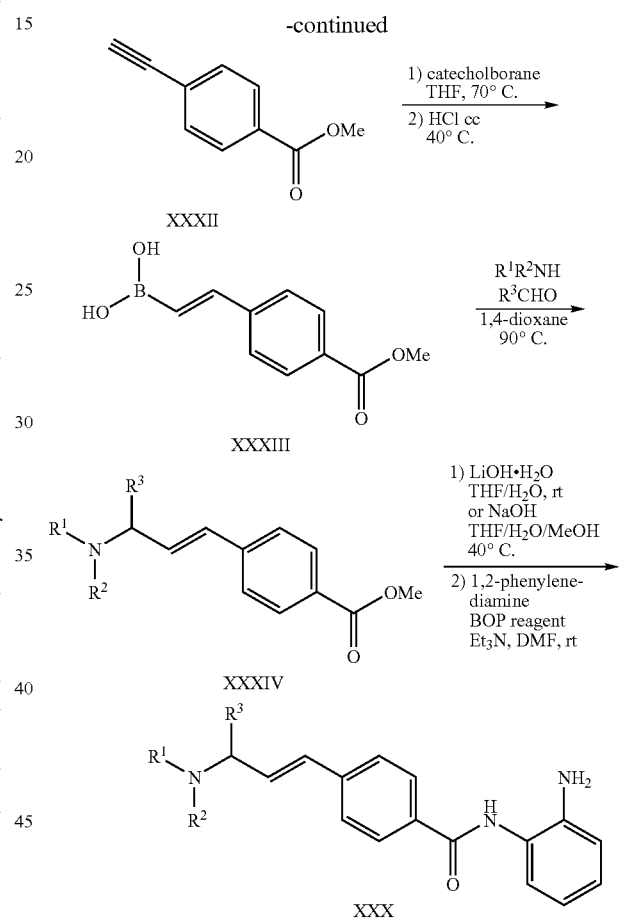

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention.

Measurement of the enzymatic activity of a histone deacetylase can be achieved using known methodologies. For example, Yoshida et al., J. Biol. Chem., 265: 17174–17179 (1990), describes the assessment of histone deacetylase enzymatic activity by the detection of acetylated histones in trichostatin A treated cells. Taunton et al., Science, 272: 408–411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with, and reduce the enzymatic activity of, a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention makes them useful research tools to study the role of histone deacetylase in various biological processes. For example, the cell proliferation inhibiting ability of the histone deacetylase inhibitors according to the invention allow the synchronization of a population of asynchronously growing cells. For example, the histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme actvity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC7, and/or HDAC-8 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/ or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1–6 saturated or unsaturated carbon atoms, or with an aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-subsbtuted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleobdes.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684–689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465–496).

Particularly preferred oligonucleotides have nucleotide sequences of from about 13 to about 35 nucleotides which include the nucleotide sequences shown in Table 1. Yet additional particularly preferred oligonucleotides have nucleotide sequences of from about 15 to about 26 nucleotides of the nucleotide sequences shown in Table 1.

TABLE 1

| Oligo | Target | Accession Number | Nucleotide Position | Sequence | position within Gene |
|---|---|---|---|---|---|
| HDAC1 AS1 | Human HDAC1 | U50079 | 1585-1604 | 5'-GAAACGTGAGGGACTCAGCA-3' | 3'-UTR |
| HDAC1 AS2 | Human HDAC1 | U50079 | 1565-1584 | 5'-GGAAGCCAGAGCTGGAGAGG-3' | 3'-UTR |
| HDAC1 MM | Human HDAC1 | U50079 | 1585-1604 | 5'-GTTAGGTGAGGCACTGAGGA-3' | 3'-UTR |
| HDAC2 AS | Human HDAC2 | U31814 | 1643-1622 | 5'-GCTGAGCTGTTCTGATTTGG-3' | 3'-UTR |
| HDAC2 MM | Human HDAC2 | U31814 | 1643-1622 | 5'-CGTGAGCACTTCTCATTTCC-3' | 3'-UTR |
| HDAC3 AS | Human HDAC3 | AF039703 | 1276-1295 | 5'-CGCTTTCCTTGTCATTGACA-3' | 3'-UTR |
| HDAC3 MM | Human HDAC3 | AF039703 | 1276-1295 | 5'-GCCTTTCCTACTCATTGTGT-3' | 3'-UTR |
| HDAC4 AS1 | Human HDAC4 | AB006626 | 514-33 | 5-GCTGCCTGCCGTGCCCACCC-3' | 5'-UTR |
| HDAC4 MM1 | Human HDAC4 | AB006626 | 514-33 | 5'-CGTGCCTGCGCTGCCCACGG-3' | 5'-UTR |
| HDAC4 AS2 | Human HDAC4 | AB006626 | 7710-29 | 5'-TACAGTCCATGCAACCTCCA-3' | 3'-UTR |
| HDAC4 MM4 | Human HDAC4 | AB006626 | 7710-29 | 5'-ATCAGTCCAACCAACCTCGT-3' | 3'-UTR |
| HDAC5 AS | Human HDAC5 | AF039691 | 2663-2682 | 5'-CTTCGGTCTCACCTGCTTGG-3' | 3'-UTR |
| HDAC6 AS | Human HDAC6 | AJ011972 | 3791-3810 | 5'-CAGGCTGGAATGAGCTACAG-3' | 3'-UTR |
| HDAC6 MM | Human HDAC6 | AJ011972 | 3791-3810 | 5'-GACGCTGCAATCAGGTAGAC-3' | 3'-UTR |
| HDAC7 AS | Human HDAC7 | AF239243 | 2896-2915 | 5'-CTTCAGCCAGGATGCCCACA-3' | 3'-UTR |
| HDAC8 AS1 | Human HDAC8 | AF230097 | 51-70 | 5'-CTCCGGCTCCTCCATCTTCC-3' | 5'-UTR |
| HDAC8 AS2 | Human HDAC8 | AF230097 | 1328-1347 | 5'-AGCCAGCTGCCACTTGATGC-3' | 3'-UTR |

The following examples are intended to further illustrate certain preferred embodiments of the invention, and are not intended to limit the scope of the invention.

EXAMPLES

Example 1

N-(2-Amino-phenyl)-4-[3-(3,4-dichloro-phenyl)-acryloyl]-benzamide (Ia)

Step 1: 4-[3-(3,4-dichloro-phenyl)-acryloyl]-benzoic acid (IIa)

To a stirred suspension at room temperature of 4-acetyl-benzoic acid (1.71 g, 10.44 mmol), 3,4-dichlorobenzaldehyde (2.05 g, 11.49 mmol) or aldehyde (1.1 equiv.) in MeOH (50 ml) was added a solution of NaOH (26.1 ml, 1N in $H_2O$). After 19 h, the reaction mixture was filtered off, rinsed with MeOH and dried to afford the title compound IIa (3.22 g, 10.03 mmol, 96% yield) as a yellow solid. $^1$H NMR (300 MHz, DMSO-$d_6$) δ(ppm): 8.35 (s, 1H), AB system ($δ_A$=8.13, $δ_B$=8.01, J=8.4 Hz, 4H), 8.12 (d, J=15.8 Hz, 1H), 7.93 (d, J=7.9 Hz, 1H), 7.76 (d, J=8.3 Hz, 1H, 7.73 (d, 15.8 Hz, 1H).

Step 2: N-(2-Amino-phenyl)-4-[3-(3,4-dichloro-phenyl)-acryloyl]-benzamide (Ia)

To a stirred solution at room temperature of IIa (300 mg, 0.93 mmol) in anhydrous DMF (15 ml) under nitrogen were added $Et_3N$ (156 µl, 1.12 mmol) and BOP reagent (454 mg, 1.03 mmol), respectively. After 30 min, a solution of 1,2-phenylenediamine (111 mg, 1.03 mmol), $Et_3N$ (391 µl, 2.80 mmol) in anhydrous DMF (2 ml) was added dropwise. After 21 h, the reaction mixture was poured into a saturated aqueous solution of $NH_4Cl$, and diluted with AcOEt. After separation, the organic layer was successively washed with sat $NH_4Cl$, $H_2O$ and brine, and concentrated. The crude residue was then purified by flash chromatography on silica gel (AcOEt/$CH_2Cl_2$:10/90→20/90) to afford the title compound Ia (237 mg, 0.58 mmol, 62% yield) as a yellow powder. $^1$H NMR (300 MHz, DMSO-$d_6$) δ(ppm): 9.90 (s, 1H), 8.40–8.30 (m, 3H), 8.25–8.10 (m, 3H), 7.97 (d, J=8.8 Hz, 1H), 7.85–7.75 (m, 2H), 7.23 (d, J=7.5 Hz, 1H), 7.03 (t, J=7.3 Hz, 1H), 6.84 (d, J=7.9 Hz, 1H), 6.65 (t, J=7.5 Hz, 1H), 4.99 (s, 2H).

Examples 2 and 10

Examples 2 and 10 (compounds Ib,Ij) were prepared using the same procedure as described for compound Ia of Example 1 (Scheme 1).

Example 3

N-(2-Amino-phenyl)-4-[3-(2,6-dichloro-phenyl)-acryloyl]benzamide (Ic)

Step 1: t-Butyl [2-(4-acetyl-benzoylamino)-phenyl]-carbamate (III)

To a stirred solution at room temperature of 4-acetylbenzoic acid (395 mg, 2.41 mmol) in anhydrous DMF (15 ml) under nitrogen were added $Et_3N$ (369 µl, 2.65 mmol) and BOP reagent (1.171 g, 2.65 mmol), respectively. After 30 min, a solution of t-butyl (2-amino-phenyl)-carbamate (551 mg, 2.65 mmol), $Et_3N$ (1.01 ml, 7.22 mmol) in anhydrous DMF (5 ml) was added dropwise. After 19 h, the reaction mixture was poured into a saturated aqueous solution of $NH_4Cl$, and diluted with AcOEt. After separation, the organic layer was successively washed with sat $NH_4Cl$, $H_2O$ and brine, dried over anhydrous $MgSO_4$, filtered and concentrated. The crude residue was then purified by flash chromatography on silica gel (AcOEt/hexane:40/60→50/50) to afford the title compound III (500 mg, 1.41 mmol, 59% yield) as a yellow solid. $^1$H NMR (300 MHz, $CDCl_3$)

δ(ppm): 9.47 (bs, 1H), 8.10–8.00 (m, 4H), 7.91 (d, J=7.9 Hz, 1H), 7.33–7.15 (m, 3H), 6.67 (s, 1H), 2.67 (s, 3H), 1.53 (s, 9H).

Step 2: t-Butyl (2-{4-[3-(2,6-dichloro-phenyl)-acryloyl]-benzoylamino}-phenyl)-carbamate (IVc)

To a stirred solution at room temperature of III (150 mg, 0.42 mmol), 2,6-dichlorobenzaldehyde (148 mg, 0.85 mmol) or aldehyde (1.5–2.0 equiv.) in MeOH (10 ml) was added a solution of NaOH (1.7 ml, 1N in $H_2O$). A pale yellow precipitate appeared. After 3 days, the reaction mixture was filtered off, rinsed with $H_2O$. The solid residue was then dissolved in AcOEt, dried over anhydrous $MgSO_4$, filtered and concentrated. The crude residue was finally purified by flash chromatography on silica gel (AcOEt/hexane:20/80→40/60) to afford the title compound IVc (185 mg, 0.36 mmol, 85% yield) as a pale yellow foam. $^1$H NMR (300 MHz, $CDCl_3$) δ(ppm): 9.48 (bs, 1H), 8.11 (s, 4H), 7.96 (d, J=17.1 Hz, 1H), 7.89 (d, J=8.8 Hz, 1H), 7.68 (d, J=16.3 Hz, 1H), 7.42 (d, J=7.9 Hz, 2H), 7.35–7.15 (m, 4H), 6.68 (s, 1H), 1.54 (s, 9H).

Step 3: N-(2-Amino-phenyl)-4-[3-(2,6-dichloro-phenyl)-acryloyl]-benzamide (Ic)

To a stirred solution at room temperature of IVc (135 mg, 0.26 mmol) in $CH_2Cl_2$ (10 ml) was added trifluoroacetic acid (2 ml, 95% in water). After 16 h, the reaction mixture was concentrated, and directly purified by flash chromatography on silica gel (AcOEt/$CH_2Cl_2$:15/85) to afford the title compound Ic (90 mg, 0.22 mmol, 83% yield) as an orange solid. $^1$H NMR (300 MHz, DMSO-$d_6$) δ(ppm): 9.89 (s, 1H), AB system ($δ_A$=8.23, $δ_B$=8.19, J=8.5 Hz, 4H), 7.90 (d, J=16.3 Hz, 1H), 7.78 (d, J=16.3 Hz, 1H), 7.67 (d, J=7.9 Hz, 2H), 7.55–7.45 (m, 1H), 7.23 (d, J=7.5 Hz, 1H), 7.03 (t, J=7.5 Hz, 1H), 6.83 (d, J=7.9 Hz, 1H), 6.64 (t, J=7.3 Hz, 1H), 5.00 (s, 2H).

Examples 4–9

Examples 4 to 9 (compounds Id–Ii) were prepared using the same procedure as described for compound Ic of Example 3 (Scheme 2).

TABLE 2

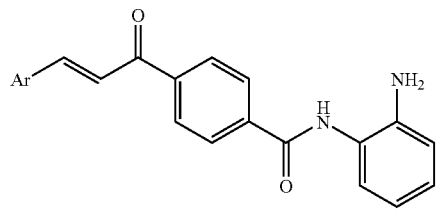

I

| Cmpd | Ar | Name | Characterization | Scheme |
|---|---|---|---|---|
| Ib | pyridin-3-yl | N-(2-Amino-phenyl)-4-(3-pyridin-3-yl-acryloyl)-benzamide | $^1$H NMR (300 MHz, DMSO-$d_6$) δ (ppm) 9.89 (s, 1H), 9.10 (s, 1H), 8.68 (d, J = 4.8 Hz, 1H), 8.44 (d, J = 7.9 Hz, 1H), AB system ($δ_A$ = 8.34, $δ_B$ = 8.20, J = 8.1 Hz, 4H), 8.19 (d, J = 15.8 Hz, 1H), 7.87 (d, J = 15.8 Hz, 1H), 7.60–7.50 (m, 1H), 7.23 (d, J = 7.9 Hz, 1H), 7.04 (t, J = 7.0Hz, 1H), 6.84 (d, J = 7.9 Hz, 1H), 6.65 (t, J = 7.3 Hz, 1H), 4.99 (s, 2H). | 1 |
| Id | 3,4,5-trimethoxyphenyl | N-(2-Amino-phenyl)-4-[3-(3,4,5-trimethoxy-phenyl)-acryloyl]-benzamide | $^1$H NMR (300 MHz, DMSO-$d_6$) δ (ppm) 9.89 (s, 1H), AB system ($δ_A$ = 8.31, $δ_B$ = 8.20, J = 8.4 Hz, 4H), 7.98 (d, J = 15.8 Hz, 1H), 7.78 (d, J =15.4 Hz, 1H), 7.31 (s, 2H), 7.23 (d, J = 7.9 Hz, 1H), 7.04 (t, J = 7.0 Hz, 1H), 6.84 (d, J = 7.5 Hz, 1H), 6.65 (t, J = 7.5Hz, 1H), 4.99 (bs, 2H), 3.92 (s, 6H), 3.77 (s, 3H). | 2 |
| Ie | 4-chlorophenyl | N-(2-Amino-phenyl)-4-[3-(4-chloro-phenyl)-acryloyl]-benzamide | $^1$H NMR (300 MHz, DMSO-$d_6$) δ (ppm) 9.90 (s, 1H), AB system ($δ_A$ = 8.33, $δ_B$ = 8.19, J = 8.4 Hz, 4H), 8.08 (d, J = 15.4 Hz, 1H), AB system ($δ_A$ = 8.02, $δ_B$ = 7.60, J = 8.6 Hz, 4H), 7.83 (d, J = 15.4 Hz, 1H), 7.22 (d, J = 7.5 Hz, 1H), 7.03 (t, J = 7.5 Hz, 1H), 6.83 (d, J = 7.9 Hz, 1H), 6.65 (t, J = 7.5 Hz, 1H), 5.00 (bs, 2H). | 2 |
| If | 2,4,6-trimethoxyphenyl | N-(2-Amino-phenyl)-4-[3-(2,4,6-trimethoxy-phenyl)-acryloyl]-benzamide | $^1$H NMR (300 MHz, DMSO-$d_6$) δ (ppm) 9.86 (bs, 1H), 8.26–8.03 (m, 5H), 7.92 (d, J = 15.8 Hz, 1H), 7.23 (d, J = 7.5 Hz, 1H), 7.03 (t, J = 7.5 Hz, 1H), 6.83 (d, J = 7.5 Hz, 1H), 6.65 (t, J = 6.8 Hz, 1H), 6.38 (s, 2H), 4.99 (bs, 2H), 3.98 (s, 6H), 3.91 (s, 3H). | 2 |

TABLE 2-continued

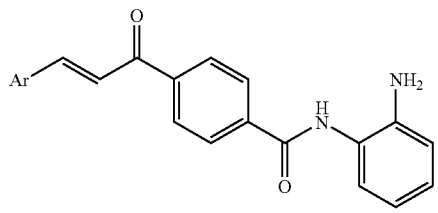

| Cmpd | Ar | Name | Characterization | Scheme |
|---|---|---|---|---|
| Ig | (3-cyclopropoxy-4-difluoromethoxy-phenyl) | N-(2-Amino-phenyl)-4-[3-(3-cyclopropoxy-4-difluoromethoxy-phenyl)-acryloyl]-benzamide | $^1$H NMR (300 MHz, DMSO-d$_6$) δ (ppm): 9.89 (s, 1H), AB system (δ$_A$ =8.31, δ$_B$ = 8.20, J = 8.1 Hz, 4H), 8.00 (d, J = 15.8 Hz, 1H), 7.83 (d, J = 15.4 Hz, 1H), ABX system (δ$_A$ = 7.30, δ$_B$ = 7.64, δ$_X$ = 7.96, J = 8.4,1.3, 0 Hz, 3H), 7.23 (d, J = 7.5 Hz, 1H), 7.17 (t, J = 74.3 Hz, 1H), 7.04 (t, J = 7.3 Hz, 1H), 6.84 (d, J = 7.5 Hz, 1H), 6.65 (t, J = 7.3 Hz, 1H), 5.00 (bs, 2H), 4.15–4.08 (m, 1H), 0.98–0.73 (m, 4H). | 2 |
| Ih | (4-trifluoromethyl-phenyl) | N-(2-Amino-phenyl)-4-[3-(4-trifluoromethyl-phenyl)-acryloyl]-benzamide | $^1$H NMR (300 MHz, DMSO-d$_6$) δ (ppm) 9.91 (bs, 1H), 8.35 (d, J = 7.9 Hz, 2H), 8.30–8.10 (m, 5H), 7.95–7.82 (m, 3H), 7.23 (d, J = 7.9 Hz, 1H), 7.04 (t, J = 7.3 Hz, 1H), 6.83 (d, J = 7.5 Hz, 1H), 6.65 (t, J = 7.3 Hz, 1H), 5.00 (bs, 2H). | 2 |
| Ii | (2,5-difluoro-phenyl) | N-(2-Amino-phenyl)-4-[3-(2,5-difluoro-phenyl)-acryloyl]-benzamide | $^1$H NMR (300 MHz, DMSO-d$_6$) δ (ppm): 9.90 (s, 1H), 8.34 (d, J = 7.9 Hz, 2H), 8.25–8.05 (m, 4H), 7.86 (d, J = 15.8 Hz, 1H), 751–7.38 (m, 2H), 7.23 (d, J = 7.5 Hz, 1H), 7.04 (t, J = 7.3 Hz, 1H), 6.84 (d, J = 7.9 Hz, 1H), 6.65 (t, J = 7.3 Hz, 1H), 5.00 (bs, 2H). | 2 |
| Ij | (3-cyclopentyloxy-4-methoxy-phenyl) | N-(2-Amino-phenyl)-4-[3-(3-cyclopentyloxy-4-methoxy-phenyl)-acryloyl]-benzamide | $^1$H NMR (300 MHz, DMSO-d$_6$) δ (ppm): 9.88 (s, 1H), AB system (δ$_A$ = 8.29, δ$_B$ = 8.19, J = 7.9 Hz, 4H), 7.88 (d, J = 15.8 Hz, 1H), 7.78 (d, J = 15.8 Hz, 1H), 7.55 (s, 1H), 7.49 (d, J = 8.4 Hz, 1H), 7.23 (d, J = 7.5 Hz, 1H), 7.08 (d, J = 8.4 Hz,1H), 7.04 (t, J = 7.5 Hz, 1H), 6.84 (d, J = 7.5 Hz, 1H), 6.65 (t, J = 7.3 Hz, 1H), 4.99 (bs, 3H), 3.86 (s, 3H), 2.10–1.55 (m, 8H). | 1 |

Example 11

N-(2-Amino-phenyl)-4-[2-(3,4,5-trimethoxy-phenyl-carbamoyl)-vinyl]-benzamide (Va)

Step 1: Methyl 4-(2-t-butoxycarbonyl-vinyl)-benzoate (VI)

To a solution of anhydrous i-Pr$_2$NH (1.76 ml, 12.49 mmol) in anhydrous THF (30 ml) stirred at 0° C. under nitrogen, was slowly added a solution of n-BuLi (5.36 ml, 13.40 mmol, 2.5 M in hexane). After 30 min, LDA was cooled to −78° C. and t-butyl acetate (1.64 ml, 12.18 mmol) was added dropewise. After 30 min, a solution of methyl 4-formylbenzoate (1.00 g, 6.09 mmol) in anhydrous THF (10 ml) was slowly added. After 2 h, a solution of 2-chloro-4,6-dimethoxy-1,3,5-triazine (1.604 g, 9.14 mmol) in anhydrous THF (10 ml) was added. Then, the temperature was allowed to warm up to room temperature overnight. A suspension appeared. The reaction mixture was poured into a saturated aqueous solution of NH$_4$Cl, and diluted with AcOEt. After separation, the organic layer was successively washed with H$_2$O and brine, dried over MgSO$_4$, filtered and concentrated. The crude product was purified by flash chromatography on silica gel (AcOEt/hexane:10/90→15/85) to give the title product VI (785 mg, 3.00 mmol, 49% yield) as a white solid. $^1$H NMR (300 MHz, CDCl$_3$) δ(ppm): AB system (δ$_A$=8.04, δ$_B$=7.57, J=8.4 Hz, 4H), 7.60 (d, J=15.4 Hz, 1H), 6.46 (d, J=15.8 Hz, 1H), 3.93 (s, 3H), 1.54 (s, 9H). $^{13}$C NMR (75 MHz, CDCl$_3$) δ(ppm): 166.72, 166.01, 142.31, 139.18, 131.33, 130.26, 127.99, 122.87, 81.11, 52.46, 28.40.

Step 2: Methyl 4-(2-carboxy-vinyl)-benzoate (VII)

To a stirred solution at room temperature of VI (745 mg, 2.84 mmol) in CH$_2$Cl$_2$ (10 ml) was added trifluoroacetc acid (6 ml, 95% in water). After 27 h, the reaction mixture was concentrated, and triturated in water. After 1 h, the suspension was filtered off, rinsed with H$_2$O, and dried to afford the title compound VII (556 mg, 2.70 mmol, 95% yield) as an off-white solid. $^1$H NMR (300 MHz, DMSO-d$_6$) δ(ppm): AB system (δ$_A$=8.01, δ$_B$=7.88, J=8.1 Hz, 4H), 7.68 (d, J=15.8 Hz, 1H), 6.70 (d, J=16.3 Hz, 1H), 3.90 (s, 3H).

Method A. Step 3: Methyl 4-[2-(benzotriazol-1-yloxycarbonyl)-vinyl]-benzoate (VIII)

To a stirred solution at room temperature of VII (264 mg, 1.28 mmol) in anhydrous DMF (10 ml) under nitrogen was added Et$_3$N (196 µl, 1.41 mmol) and BOP reagent (680 mg, 1.1.54 mmol), respectively. After few min, a precipitate appeared. After 3 h, the reaction mixture was poured into a saturated aqueous solution of NH$_4$Cl, and diluted with AcOEt. After separation, the organic layer was successively washed with sat NH$_4$Cl, H$_2$O and brine, concentrated a little bit, and hexane was added. The suspension was filtered off and rinsed with hexane. The solid was triturated in water, filtered off, rinsed with water, and dried to afford the title compound VIII (346 mg, 1.07 mmol, 84% yield) as a pale yellow solid (not stable on silica gel !). $^1$H NMR (300 MHz, CDCl$_3$) δ(ppm): 8.56 (d, J=8.3 Hz, 1H), 8.21–8.02 (m, 3H), 7.90–7.72 (m, 4H), 7.62 (t, J=7.4 Hz, 1H), 3.97 (s, 3H).

Step 4: Methyl 4-[2-(3,4,5-trimethoxy-phenylcarbamoyl)-vinyl]-benzoate (IXa)

To a stirred suspension at room temperature of VIII (150 mg, 0.46 mmol) in anhydrous CH$_2$Cl$_2$ (10 ml) under nitrogen were added Et$_3$N (194 μl, 1.39 mmol) and 3,4,5-trimethoxyaniline (94 mg, 0.51 mmol) or ArNH$_2$(1.1–1.2 equiv.), respectively. The reaction mixture was heated to 60° C. After 20 h, the reaction mixture was concentrated, diluted with AcOEt, and successively washed with a saturated aqueous solution of NH$_4$Cl, H$_2$O and brine, dried over MgSO$_4$, filtered and concentrated. The crude product was purified by flash chromatography on silica gel (AcOEt/CH$_2$Cl$_2$:15/85→20/80) to give the title product IXa (130 mg, 0.35 mmol, 75% yield) as a yellow solid. $^1$H NMR (300 MHz, acetone-d$_6$) δ(ppm): 9.42 (bs, 1H), AB system (δ$_A$=8.09, δ$_B$=7.78, J=8.1 Hz, 4H), 7.75 (d, J=15.6 Hz, 1H), 7.21 (s, 2H), 7.00 (d, J=15.8 Hz, 1H), 3.94 (s, 3H), 3.85 (s, 6H), 3.73 (s, 3H).

Step 5: 4-[2-(3,4,5-Trimethoxy-phenylcarbamoyl)-vinyl]-benzoate (Xa)

To a stirred solution at room temperature of IXa (125 mg, 0.34 mmol) in THF (5 ml) was added a solution of LiOH.H$_2$O (35 mg, 0.84 mmol) in water (5 ml). After 1.5 day, the reaction mixture was concentrated, diluted with water and acidified with 1N HCl until pH 4–5 in order to get a precipitate. After stirring for 10 min, the suspension was filtered off, rinsed with water, and dried to afford the title compound Xa (110 mg, 0.31 mmol, 91% yield) as a pale yellow solid. $^1$H NMR (300 MHz, DMSO-d$_6$) δ(ppm): 10.29 (s, 1H), AB system (δ$_A$=8.04, δ$_B$=7.76, J=8.4 Hz, 4H), 7.65 (d, J=15.8 Hz, 1H), 7.13 (s, 2H), 6.94 (d, J=15.8 Hz, 1H), 3.81 (s, 6H), 3.67 (s, 3H).

Step 6: N-(2-Amino-phenyl)-4-[2-(3,4,5-trimethoxy-phenylcarbamoyl)-vinyl]-benzamide (Va)

To a stirred solution at room temperature of Xa (110 mg, 0.31 mmol) in anhydrous DMF (3 ml) under nitrogen were added Et$_3$N (47 μl, 0.34 mmol) and BOP reagent (163 mg, 0.37 mmol), respectively. After 30 min, a solution of 1,2-phenylenediamine (37 mg, 0.34 mmol), Et$_3$N (129 μl, 0.92 mmol) in anhydrous DMF (1 ml) was added dropwise. After 3 h, the reaction mixture was poured into a saturated aqueous solution of NH$_4$Cl, and diluted with AcOEt. After separation, the organic layer was successively washed with sat NH$_4$Cl, H$_2$O and brine, dried over MgSO$_4$, filtered, and concentrated. The crude residue was then purified by flash chromatography on silica gel (AcOEt/CH$_2$Cl$_2$:50/50→80/20) to afford the title compound Va (98 mg, 0.22 mmol, 71% yield) as a yellow solid. $^1$H NMR (300 MHz, DMSO-d$_6$) δ(ppm): 10.27 (s, 1H), 9.76 (s, 1H), AB system (δ$_A$=8.09, δ$_B$=7.78, J=7.9 Hz, 4H), 7.71 (d, J=15.8 Hz, 1H), 7.22 (d, J=7.5 Hz, 1H), 7.14 (s, 2H), 7.02 (t, J=7.0 Hz, 1H), 6.95 (d, J=15.8 Hz, 1H), 6.83 (d, J=7.9 Hz, 1H), 6.65 (t, J=7.5 Hz, 1H), 4.97 (bs, 2H), 3.81 (s, 6H), 3.68 (s, 3H).

Example 12

N-(2-Amino-phenyl)-4-{2-[(pyridin-3-ylmethyl)-carbamoyl]-vinyl}-benzamide (Vb)

Method B, Step 3: Methyl 4-[2-(pyridin-3-ylmethyl)-carbamoyl)-vinyl]-benzoate (Vb)

To a stirred solution at room temperature of VIII (140 mg, 0.68 mmol) in anhydrous DMF (5 ml) under nitrogen were added Et$_3$N (104 μl, 0.75 mmol) and BOP reagent (331 mg, 0.75 mmol), respectively. After 30 min, a solution of 3-(aminomethyl)pyridine (90 μl, 0.88 mmol) or R$^1$R$^2$NH (1.2–1.3 equiv.), Et$_3$N (284 μl, 2.04 mmol) in anhydrous DMF (2 ml) was added dropwise. After 4 h, the reaction mixture was poured into a saturated aqueous solution of NH$_4$Cl, and diluted with AcOEt. After separation, the organic layer was successively washed with sat NH$_4$Cl, H$_2$O and brine, dried over MgSO$_4$, filtered, and concentrated. The crude residue was then purified by flash chromatography on silica gel (MeOH/CH$_2$Cl$_2$:5/95→7/93) to afford the title compound IXb (185 mg, 0.62 mmol, 92% yield) as a white solid. $^1$H NMR (300 MHz, CDCl$_3$) δ(ppm): 8.67–8.44 (m, 2H), AB system (δ$_A$=8.03, δ$_B$=7.55, J=8.4 Hz, 4H), 7.78–7.64 (m, 2H), 7.33–7.26 (m, 1H), 6.54 (d, J=15.8 Hz, 1H), 6.38 (bs, 1H), 4.61 (d, J=6.2 Hz, 2H), 3.92 (s, 3H).

Step 4: N-(2-Amino-phenyl)-4-{2-[(pyridin-3-ylmethyl)-carbamoyl]-vinyl}-benzamide (Vb)

The title compound Vb was obtained from IXb in two steps following the same procedure as Example 10, steps 5 and 6 (Scheme 3). $^1$H NMR (300 MHz, DMSO-d$_6$) δ(ppm): 9.74 (s, 1H), 8.79 (t, J=5.7 Hz, 1H), 8.58 (s, 1H), 8.52 (d, J=4.0 Hz, 1H), 8.06 (d, J=7.9 Hz, 2H), 7.83–7.68 (m, 3H), 7.59 (d, J=15.8 Hz, 1H), 7.41 (dd, J=7.9, 4.7 Hz, 1H), 7.21 (d, J=7.9 Hz, 1H), 7.02 (t, J=7.0 Hz, 1H), 6.83 (d, J=15.8 Hz, 1H), 6.82 (d, J=7.5 Hz, 1H), 6.64 (t, J=7.3 Hz, 1H, 4.96 (bs, 2H), 4.48 (d, J=5.7 Hz, 2H).

Examples 13–15

Examples 13 to 15 (compounds Vc–Ve) were prepared using the same procedure as described for compound Vb of Example 12 (Scheme 3).

Example 16

N-(2-Amino-phenyl)-4-[2-(2-pyridin-3-yl-ethylcarbamoyl)-vinyl]-benzamide (Vf)

Step 1: t-Butyl [2-(4-formyl-benzoylamino)-phenyl]-carbamate (XI)

To a stirred suspension at room temperature of 4-carboxybenzaldehyde (3.00 g, 19.98 mmol) in anhydrous CH$_2$Cl$_2$ (10 ml) under nitrogen were added thionyl chloride (2.19 ml, 29.97 mmol) and anhydrous DMF (387 μl, 5.00 mmol), respectively. The reaction mixture was refluxed for 5 h. Then, the reaction mixture was allowed to cool to room temperature, concentrated, and diluted with anhydrous CH$_2$Cl$_2$ (20 ml) under nitrogen. This solution was canulated into a cooled mixture at −20° C. of t-butyl (2-aminophenyl)-carbamic ester (4.575 g, 21.98 mmol), Et$_3$N (8.36 ml, 59.95 mmol in anhydrous CH$_2$Cl$_2$ (50 ml) under nitrogen. After 1 h, the reaction mixture was allowed to warm up to room temperature. After 1 h, it was poured into a saturated aqueous solution of NH$_4$Cl, and extracted with CH$_2$Cl$_2$. The combined organic layer was successively dried over MgSO$_4$, filtered, and concentrated. The crude residue was then purified by flash chromatography on silica gel (AcOEt/hexane:30/70→40/60) to afford the title compound XI (4.80 g, 14.11 mmol, 71% yield) as a pale yellow solid. $^1$H NMR (300 MHz, CDCl$_3$) δ(ppm): 10.11 (s, 1H), 9.58 (bs, 1H), AB system (δ$_A$=8.14, δ$_B$=7.99, J=8.1 Hz, 4H), 7.89 (d, J=7.9 Hz, 1H), 7.35–7.10 (m, 3H), 6.75 (s, 1H), 1.53 (s, 9H).

Step 2: Methyl 3-[4-(2-t-butoxycarbonylamino-phenylcarbamoyl)-phenyl]-acrylate (XII)

A stirred suspension of compound XI (500 mg, 1.47 mmol), methyl (triphenyl-phosphoranylidene)acetate (590 mg, 1.76 mmol) in anhydrous toluene (20 ml) was heated at 90° C. under nitrogen. After 2 days, the reaction mixture was concentrated and directly purified by flash chromatography on silica gel (AcOEt/hexane:30/70→40/60) to afford the title compound XII (568 mg, 1.43 mmol, 97% yield) as a pale yellow foam. $^1$H NMR (300 MHz, CDCl$_3$) δ(ppm): 9.32 (bs, 1H), AB system (δ$_A$=7.99, δ$_B$=7.62, J=8.4 Hz, 4H), 7.87 (d, J=7.9 Hz, 1H), 7.73 (s, J=15.8 Hz, 1H), 7.32–7.13 (m, 3H), 6.69 (bs, 1H), 6.53 (d, J=16.3 Hz, 1H), 3.83 (s, 3H), 1.53 (s, 9H).

Step 3: 3-[4-(2-t-Butoxycarbonylamino-phenylcarbamoyl)-phenyl]-acrylic acid (XIII)

To a stirred solution at room temperature of compound XII (560 mg, 1.41 mmol) in THF (20 ml) was added a solution of LiOH.H$_2$O (148 mg, 3.53 mmol) in water (20 ml). After 23 h, the reaction mixture was concentrated, diluted with water and acidified with 1N HCl until pH 4–5 in order to get a white precipitate. After stirring for 15 min, the suspension was filtered off, rinsed with water, and dried to afford the title compound XIII (495 mg, 1.29 mmol, 92% yield) as a white solid. $^1$H NMR (300 MHz, DMSO-d$_6$) δ(ppm): 9.92 (s, 1H), 8.72 (bs, 1H), AB system (δ$_A$=8.02, δ$_B$=7.90, J=7.9 Hz, 4H), 7.69 (d, J=16.3 Hz, 1H), 7.62–7.53 (m, 2H), 7.30–7.13 (m, 2H), 6.72 (d, J=16.3 Hz, 1H), 1.48 (s, 9H)

Step 4: t-Butyl (2-{4-[2-(2-pyridin-3-yl-ethylcarbamoyl)vinyl]-benzoylamino}-phenyl)-carbamate (XIVf)

To a stirred solution at room temperature of compound XIII (80 mg, 0.21 mmol) in anhydrous DMF (3 ml) under nitrogen were added Et$_3$N (35 μl, 0.25 mmol) and BOP reagent (102 mg, 0.23 mmol), respectively. After 30 min, a solution of 3-(2-aminoethyl)pyridine (51 mg, 0.42 mmol) or RXH (1.5–2.0 equiv.), Et$_3$N (87 μl, 0.63 mmol) in anhydrous DMF (1 ml) was added dropwise. After 3–5 h, the reaction mixture was poured into a saturated aqueous solution of NH$_4$Cl, and diluted with AcOEt. After separation, the organic layer was successively washed with sat NH$_4$Cl, H$_2$O and brine, dried over MgSO$_4$, filtered, and concentrated to afford the title compound XIVf. It was used in the next step without further purification.

Step 5: N-(2-Amino-phenyl)-4-[2-(2-pyridin-3-yl-ethylcarbamoyl)-vinyl]-benzamide (Vf)

To a stirred solution at room temperature of XIVf in CH$_2$Cl$_2$ (15 ml) was added trifluoroacetic acid (2 ml, 95% in water). After 18 h, the reaction mixture was concentrated, dissolved in water, and neutralized with a saturated aqueous solution of NaHCO$_3$ until a pH=7. A pale yellow precipitate appeared. After few minutes, the suspension was filtered off, rinsed with H$_2$O, and dried to afford the title compound Vf (69 mg, 0.18 mmol, 85% yield for two steps) as a pale yellow solid. $^1$H NMR (300 MHz, DMSO-d$_6$) δ(ppm): 9.72 (s, 1H), 8.53–8.41 (m, 2H), 8.29 (t, J=5.5 Hz, 1H), 8.05 (d, J=8.4 Hz, 2H), 7.80–7.63 (m, 3H), 7.51 (d, J=15.8 Hz, 1H), 7.37 (dd, J=7.5, 4.8 Hz, 1H), 7.21 (d, J=7.5 Hz, 1H), 7.02 (t, J=7.5 Hz, 1H), 6.82 (d, J=7.5 Hz, 1H), 6.76 (d, J=15.8 Hz, 1H), 6.64 (t, J=7.3 Hz, 1H), 4.95 (bs, 2H), 3.51 (dd, J=6.8 Hz, 2H), 2.86 (t, J=6.8 Hz, 2H).

Examples 17–26

Examples 17 to 26 (compounds Vg–Vp) were prepared using the same procedure as described for compound Vf of Example 16 (Scheme 4).

TABLE 3

V

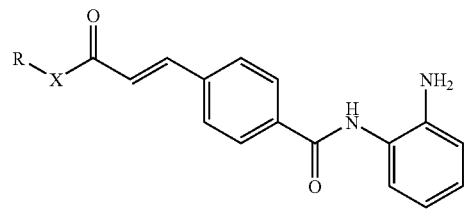

| Cmpd | Rx- | Name | Characterization | Scheme |
|---|---|---|---|---|
| Vc | (3,4,5-trimethoxybenzyl) | N-(2-Amino-phenyl)-4-[2-(3,4,5-trimethoxy-benzylcarbamoyl)-vinyl]-benzamide | $^1$H NMR (300 MHz, DMSO-d$_6$) δ (ppm) 9.73 (s, 1H), 8.64 (t, J = 5.7 Hz, 1H), AB system (δ$_A$ = 8.06, δ$_B$ = 7.74, J = 8.1 Hz, 4H), 7.58 (d, J = 15.8 Hz, 1H), 7.21 (d, J = 7.5 Hz, 1H), 7.02 (t, J = 7.3 Hz, 1H), 6.85 (d, J = 15.8 Hz, 1H), 6.82 (d, J = 7.0 Hz,1H), 6.68 (s, 2H), 6.64 (t, J = 7.5 Hz, 1H), 4.95 (bs, 2H), ), 4.39 (d, J = 5.7 Hz, 2H), 3.81 (s, 6H), 3.67 (s, 3H). | 3 |

TABLE 3-continued

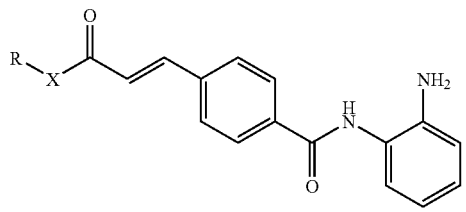

| Cmpd | Rx- | Name | Characterization | Scheme |
|---|---|---|---|---|
| Vd | phenoxyethyl-NH- | N-(2-Amino-phenyl)-4-[2-(2-phenoxy-ethylcarbamoyl)-vinyl]-benzamide | $^1$H NMR (300 MHz, DMSO-$d_6$) δ (ppm) 9.73 (s, 1H), 8.48 (t, J = 5.3 Hz, 1H), AB system ($δ_A$ = 8.06, $δ_B$ = 7.74, J = 8.3 Hz, 4H), 7.56 (d, J = 15.8 Hz, 1H), 7.34 (t, J = 7.9 Hz, 2H), 7.21 (d, J = 7.5 Hz, 1H), 7.10–9.90 (m, 4H), 6.85 (d, J = 15.4 Hz, 1H), 6.82 (d, J = 7.0 Hz, 1H), 6.64 (t, J = 7.3 Hz, 1H), 4.95 (bs, 2H), ), 4.10 (t, J = 5.3 Hz, 2H), 3.62 (quadruplet, J = 5.3 Hz, 2H). | 3 |
| Ve | morpholin-4-yl | N-(2-Amino-phenyl)-4-(3-morpholin-4-yl-3-oxo-propenyl)-benzamide | $^1$H NMR (300 MHz, DMSO-$d_6$) δ (ppm) 9.75 (s, 1H), AB system ($δ_A$ = 8.05, $δ_B$ = 7.90, J = 8.1 Hz, 4H), 7.61 (d, J = 15.4 Hz, 1H), 7.43 (d, J = 15.4 Hz, 1H), ), 7.20 (d, J = 7.9 Hz, 1H), 7.02 (t, J = 7.0 Hz, 1H), 6.82 (d, J = 7.9 Hz, 1H), 6.64 (t, J = 7.5 Hz, 1H), 4.95 (bs, 2H),3.90–3.55 (m, 8H). | 3 |
| Vg | pyridin-3-ylmethoxy | Pyridin-3-ylmethyl 3-[4-(2-amino-phenylcarbamoyl)-phenyl]-acrylic ester | $^1$H NMR (300 MHz, DMSO-$d_6$) δ (ppm) 9.75 (s, 1H), 8.72 (s, 1H), 8.61 (bs, 1H), AB system ($δ_A$ = 8.05, $δ_B$ = 7.92, J = 7.5 Hz, 4H, included 1H), 7.82 (d, J = 16.3 Hz, 1H), 7.55–7.43 (m, 1H), 7.21 (d, J = 7.5 Hz, 1H), 7.01 (t, J = 7.3 Hz, 1H), 6.88 (d, J = 15.8 Hz,1H), 6.82 (d, J = 7.5 Hz, 1H), 6.63 (t, J = 7.0 Hz, 1H), 5.33 (s, 2H), 4.95 (bs, 2H). | 4 |
| Vh | indan-2-ylamino | N-(2-Amino-phenyl)-4-[2-(indan-2-ylcarbamoyl)-vinyl]-benzamide | $^1$H NMR (300 MHz, DMSO-$d_6$) δ (ppm) 9.71 (s, 1H), 8.51 (d, J = 7.0 Hz, 1H), AB system ($δ_A$ = 8.04, $δ_B$ = 7.71, J = 8.4 Hz, 4H), 7.54 (d, J = 15.8 Hz, 1H), 7.36–7.14 (m, 5H), 7.01 (t, J = 7.3 Hz, 1H), 6.82 (d, J = 7.5 Hz, 1H), 6.77 (d, J = 16.3 Hz, 1H), 6.63 (t, J = 7.5Hz, 1H), 4.94 (bs, 2H), 4.71–4.57 (m, 1H), 3.28 (dd, J = 16.0, 7.3 Hz, 2H), 2.87 (dd, J = 16.3, 5.3 Hz, 2H). | 4 |
| Vi | 2-pyridin-2-yl-ethylamino | N-(2-Amino-phenyl)-4-[2-(2-pyridin-2-yl-ethylcarbamoyl)-vinyl]-benzamide | $^1$H NMR (300 MHz, DMSO-$d_6$) δ (ppm): 9.72 (s, 1H), 8.56 (d, J = 4.4 Hz, 1H), 8.28 (t, J = 5.5 Hz, 1H), 8.05 (d, J = 8.4 Hz, 2H), 7.82–7.66 (m, 3H), 7.52 (d, J = 15.8 Hz, 1H), 7.40–7.15 (m, 3H), 7.02 (t, J = 7.3 Hz, 1H), 6.82 (d, J = 8.4 Hz, 1H), 6.77 (d, J = 15.8 Hz, 1H), 6.64 (t,J = 7.3 Hz, 1H), 4.95 (s, 2H), 3.61 (quadruplet, J = 6.6 Hz, 2H), 2.99 (t, J = 7.2 Hz, 2H). | 4 |
| Vj | 2-(1H-indol-3-yl)-ethylamino | N-(2-Amino-phenyl)-4-{2-[2-(1H-indol-3-yl)-ethylcarbamoyl]-vinyl}-benzamide | $^1$H NMR (300 MHz, DMSO-$d_6$) δ (ppm): 10.85 (bs, 1H), 9.73 (bs, 1H), 8.31 (t, J = 5.6 Hz, 1H), AB system ($δ_A$ = 8.06, $δ_B$ = 7.73, J = 8.0 Hz, 4H), 7.61 (d, J = 9.0 Hz, 1H), 7.55 (d, J = 15.0 Hz, 1H), 7.39 (d, J = 9.0 Hz, 1H), 7.28–7.15 (m, 2H), 7.11 (t,J = 7.5 Hz, 1H), 7.03 (d, J = 9.0 Hz, 1H), 6.83 (d, J = 7.5 Hz, 1H), 6.81 (d, J = 15.0 Hz, 1H), 6.64 (t, J = 7.3 Hz, 1H), 4.94 (s, 2H), 3.54 (quadruplet, J = 6.7 Hz, 2H), 2.94 (t, J = 6.8 Hz, 2H). | 4 |
| Vk | 4-(3,4-dimethoxyphenyl)-piperidin-1-yl | N-(2-Amino-phenyl)-4-{3-[4-(3,4-dimethoxy-phenyl)-piperidin-1-yl]-3-oxo-propenyl}-benzamide | $^1$H NMR (300 MHz, DMSO-$d_6$) δ (ppm) 9.74 (s, 1H), AB system ($δ_A$ = 8.05, $δ_A$ = 7.91, J = 8.1 Hz, 4H), 7.60 (d, J = 15.8 Hz, 1H), 7.49 (d, J = 15.4 Hz, 1H), ), 7.21 (d, J = 7.5 Hz, 1H), 7.02 (t, J = 7.0 Hz, 1H), 6.95–6.75 (m, 4H), 6.64 (t,J = 7.3 Hz, 1H), 4.95 (bs, 2H), 4.70 (bd, J = 11.9 Hz, 1H), 4.50 (bd, J = 12.3 Hz, 1H), 3.79 and 3.75 (2s, 6H), 3.22 (bt, J = 12.3 Hz, 1H), 2.88–2.70 (m, 2H), 1.96–1.80 (m, 2H), 1.75–1.47 (m, 2H). | 4 |
| Vl | 2-pyridin-3-yl-pyrrolidin-1-yl | (rac)-N-(2-Amino-phenyl)-4-[3-oxo-3-(2-pyridin-3-yl-pyrrolidin-1-yl)-propenyl]-benzamide | $^1$H NMR (300 MHz, DMSO-$d_6$) δ (ppm) mixture of rotamers, 9.75 and 9.67 (2s, 1H), 8.55–8.45 (m, 2H), 8.05–6.58 (m, 12H), 5.60–5.55 and 5.25–5.20 (2m, 1H), 5.00–4.90 (m, 2H), 4.15–3.65 (m, 2H), 2.50–2.28 (m, 1H), 2.10–1.75 (m, 3H). | 4 |

TABLE 3-continued

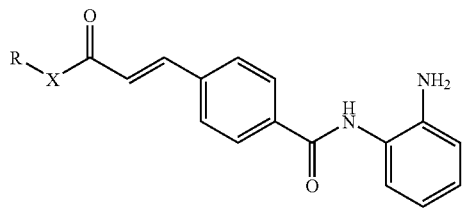

V

| Cmpd | Rx- | Name | Characterization | Scheme |
|---|---|---|---|---|
| Vm | pyridin-2-yl-piperazinyl-CH= | N-(2-Amino-phenyl)-4-[3-oxo-3-(4-pyridin-2-yl-piperazin-1-yl)-propenyl]-benzamide | $^1$H NMR (300 MHz, DMSO-$d_6$) δ (ppm) 9.75 (s, 1H), 8.18 (d, J = 3.5 Hz, 1H), AB system ($δ_A$ = 8.06, $δ_B$ = 7.92, J = 8.1 Hz, 4H), 7.70–7.55 (m, 2H) 7.49 (d, J = 15.4 Hz, 1H),), 7.21 (d, J = 7.5 Hz, 1H), 7.02 (t, J = 7.5 Hz, 1H), 6.92 (d, J = 8.8 Hz, 1H), 6.83 (d, J = 7.9 Hz, 1H), 6.72 (t, J = 6.2 Hz, 1H), 6.64 (t, J = 7.5 Hz, 1H), 4.95 (bs, 2H), 4.00–3.50 (m, 8H). | 4 |
| Vn | N-(2-cyanoethyl)-N-(pyridin-3-ylmethyl)- | N-(2-Amino-phenyl)-4-{2-[(2-cyano-ethyl)-pyridin-3-ylmethyl-carbamoyl]-vinyl}-benzamide | $^1$H NMR (300 MHz, DMSO-$d_6$) δ (ppm) mixture of rotamers, 9.75 and 9.72 (2s, 1H), 8.65–8.45 (m, 2H), 8.15–7.80 (m, 4H), 7.78–7.62 (m, 2H), 7.55–7.35 (m, 2H), 7.21 (d, J = 7.5 Hz, 1H), 7.02 (t, J = 7.5 Hz, 1H), 6.83 (d, J = 7.9 Hz, 1H), 6.64 (t, J = 7.3 Hz, 1H), 5.02(bs, 1H), 4.95 (bs, 2H), 4.74 (bs, 1H), 3.93 (bs, 1H), 3.71 (t, J = 6.2 Hz, 1H),), 2.92 (t, J = 6.2 Hz, 1H),), 2.86 (t, J = 6.2 Hz, 1H). | 4 |
| Vo | bis(pyridin-3-ylmethyl)- | N-(2-Amino-phenyl)-4-[2-(bis-pyridin-3-ylmethyl-carbamoyl)-vinyl]-benzamide | $^1$H NMR (300 MHz, DMSO-$d_6$) δ (ppm) 9.73 (s, 1H), 8.60–8.45 (m, 4H), AB system ($δ_A$ = 8.03, $δ_B$ = 7.87, J = 8.4 Hz, 4H), 7.80–7.63 (m, 3H), 7.49 (d, J = 15.4 Hz, 1H), 7.45–7.32 (m, 2H), 7.20 (d, J = 7.5 Hz, 1H), 7.01 (t, J = 7.0 Hz, 1H), 6.82 (d, J = 7.5Hz, 1H), 6.63 (t, J = 7.3 Hz, 1H), 4.97 and 4.95 (2s, 4H), 4.70 (s, 2H). | 4 |
| Vp | (1S,2R)-2-hydroxy-indan-1-yl | (−)-(1S,2R)-N-(2-Amino-phenyl)-4-[2-(2-hydroxy-indan-1-ylcarbamoyl)-vinyl]-benzamide | $^1$H NMR (300 MHz, DMSO-$d_6$) δ (ppm) 9.73 (s, 1H), 8.26 (d, J = 8.8 Hz, 1H), AB system ($δ_A$ = 8.07, $δ_B$ = 7.75, J = 8.1 Hz, 4H), 7.62 (d, J = 15.4 Hz, 1H), 7.35–7.15 (m, 5H), 7.13 (d, J = 15.8 Hz, 1H), 7.02 (t, J = 7.5 Hz, 1H), 6.83 (d, J = 7.0 Hz, 1H), 6.64 (t, J = 7.5 Hz, 1H), 5.39 (dd, J = 8.4, 4.8 Hz, 1H), 5.19 (d, J = 4.0 Hz, 1H), 4.97 (bs, 2H), 4.58–4.46 (m, 1H), 3.14 (dd, J = 16.3, 4.8 Hz, 1H), 2.88 (d, J = 15.8, 5.3 Hz, 1H). | 4 |

Example 27

N-(2-Amino-phenyl)-4-[3-(3-cyclopentyloxy-4-methoxy-phenylamino)-propenyl]-benzamide (XVa)

Step 1: t-Butyl {2-[4-(3-oxo-propenyl)-benzoylamino]-phenyl}-carbamate (XVI)

A stirred suspension of compound XI (4.00 g, 11.75 mmol), (triphenylphosphoranylidene)-acetaldehyde (3.60 g, 11.83 mmol) in anhydrous toluene (100 ml) was heated at 80° C. under nitrogen. After 2 days, the reaction mixture was concentrated and directly purified by flash chromatography on silica gel (AcOEt/hexane:30/70) to afford the title compound XVI (3.70 g, 10.10 mmol, 86% yield) as a yellow sticky solid (slightly contaminated with the diene). $^1$H NMR (300 MHz, CDCl$_3$) δ(ppm): 9.75 (d, J=7.8 Hz, 1H), 9.49 (bs, 1H), AB system ($δ_A$=8.03, $δ_B$=7.65, J=8.4 Hz, 4H), 7.85–7.72 (m, 1H), 7.52 (d, J=15.6 Hz, 1H), 7.33–7.05 (m, 3H), 7.05–6.90 (m, 1H), 6.78 (dd, J=15.6, 7.8 Hz, 1H), 1.53 (s, 9H).

Step 2: t-Butyl (2-{4-[3-(3-cyclopentyloxy-4-methoxy-phenylamino)-propenyl]-benzoylamino}-phenyl)-carbamate (XVIIa)

To a stirred solution at room temperature of compound XVI (210 mg, 0.57 mmol), 3-cyclopentyloxy-4-methoxy-aniline (125 mg, 0.60 mmol) or ArNH$_2$ (1.05–1.2 equiv.) in anhydrous THF (7 ml) under nitrogen were added dibutyltin dichloride (3.5 mg, 0.01 mmol). After 10 min, phenylsilane (78 μl, 0.63 mmol) was added dropwise. After 3 days, the reaction mixture was concentrated and directly purified by flash chromatography on silica gel (AcOEt/hexane:30/70→50/50) to afford the title compound XVIIa as a yellow sticky oil.

Step 3: N-(2-Amino-phenyl)-4-[3-(3-cyclopentyloxy-4-methoxy-phenylamino)-propenyl]-benzamide (XVa)

To a stirred solution at room temperature of XVIIa in CH$_2$Cl$_2$ (30 ml) was added trifluoroacetic acid (5 ml, 95% in water). After 16 h, the reaction mixture was concentrated, dissolved in water, and basified with a aqueous solution of NaOH (1N) until a pH=8. A beige precipitate appeared. After 15 min, the suspension was filtered off, rinsed with H$_2$O, and air-dried. The crude product was purified by flash chromatography on silica gel (AcOEt/CH$_2$Cl$_2$:15/85→20/80+ε NH$_4$OH) to afford the title compound XVa (145 mg, 0.32 mmol, 55% yield for two steps) as a yellow solid. $^1$H NMR (300 MHz, DMSO-d$_6$) δ(ppm): mixture of rotamers, 9.67 and 9.63 (2s, 1H), 7.98 (d, J=7.9 Hz, 2H), 7.57 and 7.51 (2d, J=7.9 Hz, 2H), 7.20 (d, J=7.9 Hz, 1H), 7.01 (t, J=7.7 Hz, 1H), 6.82 (d, J=7.9 Hz, 1H), 6.77–6.67 (m, 2H), 6.63 (t, J=7.5 Hz, 1H), 6.54 (dt, J=16.3, 5.2 Hz, 1H), 6.35 and 6.30 (2d, J=2.0 Hz, 1H), 6.15 and 6.06 (2dd, J=8.6, 2.0 Hz, 1H), 5.98 and 5.57 (2t, J=5.5 Hz, 1H), 4.92 (bs, 2H), 4.78–4.63 (m, 1H), 4.32 and 3.87 (2d, J=5.6 Hz, 2H), 3.65 and 3.62 (2s, 3H), 1.95–1.45 (m, 8H).

Examples 28–32

Examples 28 to 32 (compounds XVb–XVf) were prepared using the same procedure as described for compound XVa of Example 27 (Scheme 5).

Example 33

N-(2-Amino-phenyl)-4-[3-(4-tolyl-sulfonylamino)-propenyl]-benzamide (XVg)

Step 1: t-Butyl {2-[4-(3-hydroxy-propenyl)-benzoylamino]-phenyl}-carbamate (XVIII)

To a stirred solution of compound XVI (1.00 g, 2.79 mmol) in ethanol (15 ml) under nitrogen was added sodium borohydride (110 mg, 2.73 mmol). After 5 min, the reaction mixture was quenched with water and diluted with AcOEt. After separation the organic layer was successively washed with brine, dried over MgSO$_4$, filtered, and concentrated. The crude residue was then purified by flash chromatography on silica gel (AcOEt/hexane:40/60) to afford the title compound XVIII (910 mg, 2.29 mmol, 82% yield) as a pale yellow solid (slightly contaminated with the diene). $^1$H NMR (300 MHz, CDCl$_3$) δ(ppm): 9.20 (s, 1H), 7.90 (d, J=7.8 Hz, 2H), 7.75 (d, J=7.5 Hz, 1H), 7.43 (d, J=8.4 Hz, 2H), 7.32–7.08 (m, 3H), 6.94 (s, 1H), 6.65 (d, J=15.9 Hz, 1H), 6.45 (td, J=15.9, 5.4 Hz, 1H), 4.35 (d, J=5.4 Hz, 2H), 1.92 (s, 1H), 1.51 (s, 9H).

Step 2: t-butyl (2-{4-[3-(4-tolyl-sulfonylamino)-propenyl]-benzoylamino}-phenyl)-carbamate (XVIIg)

To a stirred solution of N-Boc-4-tolylsulfonamide (221 mg, 0.81 mmol) and PPh$_3$ (427 mg, 1.63 mmol) in anhydrous THF (4 ml) under nitrogen was successively added a solution of compound XVIII (200 mg, 0.54 mmol) in anhydrous THF (1 ml) and diethyl azodicarboxylate (DEAD) (214 µl, 1.36 mmol). After 16 h, the reaction mixture was quenched with water and diluted with AcOEt. After separation the organic layer was successively washed with water and brine, dried over MgSO$_4$, filtered, and concentrated. The crude residue was then purified by flash chromatography on silica gel (AcOEt/hexane:40/60) to afford the title compound XVIIg (337 mg).

Step 3: N-(2-Amino-phenyl)-4-[3-(4tolyl-sulfonylamino)-propenyl]-benzamide (XVg)

To a stirred solution at room temperature of XVIIg in CH$_2$Cl$_2$ (20 ml) was added trifluoroacetic acid (2 ml, 95% in water). After 16 h, the reaction mixture was concentrated, dissolved in water, and basified with a aqueous saturated solution of NaHCO$_3$. The aqueous layer was extracted with AcOEt. The combined organic layer was successively washed with brine, dried over MgSO$_4$, filtered, and concentrated. The crude residue was solubilized with a minimum of a mixture of AcOEt/MeOH (95/5) and coprecipitated with hexane. An off-white precipitate appeared. After few minutes, the suspension was filtered off, rinsed with hexane and dried to give the title compound XVg (173 mg, 0.41 mmol, 76% yield for two steps) as an off-white solid. $^1$H NMR: (300 MHz, DMSO-d$_6$) δ(ppm): 9.64 (s, 1H), AB system (δ$_A$=7.93, δ$_B$=7.72, J=8.4 Hz, 4H), 7.84 (s, 1H), 7.41 (t, J=8.4 Hz, 4H), 7.16 (d, J=7.8 Hz, 1H), 6.97 (t, J=7.5 Hz, 1H), 6.77 (d, J=7.5 Hz, 1H), 6.59 (t, J=7.8 Hz, 1H), 6.52 (d, J=15.6 Hz, 1H), 6.21 (dt, J=15.6, 5.7 Hz, 1H), 4.89 (s, 2H), 3.60 (bs, 2H), 2.08 (s, 3H).

Example 34

N-(2-Amino-phenyl)-4-{3-[(pyridin-3-ylmethyl)-amino]propenyl}-benzamide (XVh)

Step 1: Methyl 4-(3-oxo-propenyl)-benzoate (XIX)

Method A: A stirred suspension of compound methyl 4-formylbenzoate (4.00 g, 24.37 mmol), (triphenylphosphoranylidene)-acetaldehyde (7.56 g, 24.85 mmol) in anhydrous toluene (100 ml) was heated at 80–90° C. under nitrogen. After 1 day, the reaction mixture was concentrated and directly purified by flash chromatography on silica gel (AcOEt/hexane:20/80□30/70) to afford the title compound XIX (2.52 g, 13.25 mmol, 54% yield) as a pale yellow solid (slightly contaminated with the diene). $^1$H NMR (500 MHz, CDCl$_3$) δ(ppm): 9.76 (d, J=7.3 Hz, 1H), AB system (δ$_A$=8.11, δ=7.64, J=8.1 Hz, 4H), 7.51 (d, J=15.6 Hz, 1H), 6.79 (dd, J=15.8, 7.6 Hz, 1H), 3.95 (s, 3H).

Method B: To a vigorously stirred emulsion at room temperature of TDA-1 (6.278 g, 19.41 mmol) and an aqueous solution of 10% of potassium carbonate (100 ml) in CH$_2$Cl$_2$ (100 ml) were added (1,3-dioxolan-2-yl)methyltriphenylphosphonium bromide (10 g, 23.29 mmol) and methyl 4-formylbenzoate (3.187 g, 19.41 mmol), respectively. After stirring for 18 h, the reaction mixture was extracted with CH$_2$Cl$_2$ and the combined organic layer was concentrated. Then, an aqueous solution of 10% HCl (100 ml) was added and the mixture stirred overnight at room temperature. The reaction mixture was diluted with water and extracted with CH$_2$Cl$_2$. The combined organic layer was successively dried over MgSO$_4$, filtered, and concentrated. The crude residue was then purified by flash chromatography on silica gel (AcOEt/hexane:20/80□30/70) and triturated in AcOEt/hexane, to afford the title compound XIX (2.50 g, 13.14 mmol, 68% yield) as a crystalline solid (pure trans geometry and free of diene).

Step 2: Methyl 4-{3-[(pyridin-3-ylmethyl)-amino]-propenyl}-benzoate (XXh)

A solution at room temperature of compound XIX (300 mg, 1.58 mmol) and 3-(aminomethyl)pyridine (193 µl, 0.60 mmol) or RNH$_2$ (1.1–1.2 equiv.) in anhydrous dichloromethane (15 ml) under nitrogen was stirred for 1 h, and sodium triacetoxyborohydride (401 mg, 1.89 mmol) was added. After 64 h, the reaction mixture was quenched with an aqueous solution of K$_2$CO$_3$ (10%) and extracted with dichloromethane. The combined organic layer was dried over MgSO$_4$, filtered, and concentrated. The crude residue was then purified by flash chromatography on silica gel (MeOH/CH$_2$Cl$_2$:5/95+ε NH$_4$OH) to afford the title compound XXh (188 mg, 0.66 mmol, 42% yield) as a dark yellow oil.

Step 3: 4-[3-(tert-Butoxycarbonyl-pyridin-3-ylmethyl-amino)-propenyl]-benzoic acid (XXIh)

To a stirred solution at room temperature of XXh (187 mg, 0.66 mmol) in 1,4-dioxane (7 ml) were added (Boc)$_2$O (173 mg, 0.80 mmol) and an aqueous solution of NaOH (3.3 ml, 1N), respectively. After 24 h, the reaction mixture was concentrated, diluted in water, and neutralized (pH=6–7) with a aqueous solution of HCl (1N). The resulting pale yellow suspension was extracted with dichloromethane. The combined organic layer was dried over MgSO$_4$, filtered and concentrated to afford the title compound XXIh (160 mg, 0.43 mmol, 66% yield) as a yellow solid.

Step 4: t-Butyl {3-[4-(2-amino-phenylcarbamoyl)-phenyl]-allyl}-pyridin-3-ylmethyl-carbamate (XXIIh)

The title compound XXIIh (Example 34) was obtained from XXIh as pale-yellow foam in one step following the same procedure as in Example 11, step 6.

Step 5: N-(2-Amino-phenyl)-4-{3-[(pyridin-3-ylmethyl)-amino]-propenyl}-benzamide (XVh)

To a stirred solution at room temperature of XXIIh (77 mg, 0.17 mmol) in dichloromethane (10 ml) was added TFA (2 ml, 95% in water). After 4.5 h, the reaction mixture was concentrated, diluted in water, basified (pH=9) with a aqueous solution of NaOH (1N), and extracted with dichloromethane. The combined organic layer was dried over MgSO$_4$, filtered and concentrated. The crude residue was then purified by flash chromatography on silica gel (MeOH/CH$_2$Cl$_2$:10/90+ε NH$_4$OH) to afford the title compound XVh (35 mg, 0.10 mmol, 58% yield) as a yellow powder. $^1$H NMR: (400 MHz, DMSO-d$_6$) δ (ppm): 9.64 (s, 1H), 8.55 (s, 1H), 8.44 (d, J=3.9 Hz, 1H), AB system ($δ_A$=7.94, $δ_B$=7.55, J=8.0 Hz, 4H), 7.78 (d, J=7.4 Hz, 1H), 7.36 (dd, J=7.0, 5.1 Hz, 1H), 7.16 (d, J=7.4 Hz, 1H), 6.98 (t, J=7.4 Hz, 1H), 6.79 (d, J=7.8 Hz, 1H), 6.65–6.55 (m, 2H), 2.51 (dt, J=16.0, 5.9 Hz, 1H), 4.93 (bs, 2H), 3.77 (s, 2H).

Examples 35–36

Examples 35 to 36 (compounds XVi–XVj) were prepared using the same procedure as described for compound XVh of Example 34 (Scheme 7, Pathway B).

TABLE 4

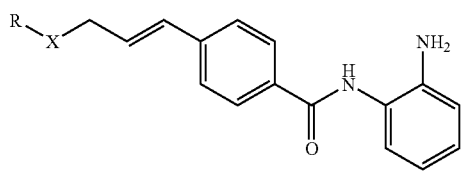

XV

| Cmpd | Rx- | Name | Characterization | Scheme |
|---|---|---|---|---|
| XVb | MeO, MeO, OMe-phenyl-NH- | N-(2-Amino-phenyl)-4[3-(3,4,5-trimethoxy-phenylamino)-propenyl]-benzamide | $^1$H NMR (300 MHz, CDCl$_3$) δ (ppm): 7.94 (m, 1H), AB system ($δ_A$ = 7.85, $δ_B$ = 7.45, J = 8.4 Hz, 4H), 7.33 (d, J = 8.1 Hz, 1H), 7.09 (t, J = 7.2 Hz, 1H), 6.90–6.78 (m, 2H), 6.69 (d, J = 15.9 Hz, 1H), 6.45 (td, J = 15.9, 5.7 Hz, 1H), 6.95 (s, 2H), 3.96 (d, J = 5.7Hz, 2H), 3.82 (s, 6H), 3.77 (s, 3H). | 5 |
| XVc | benzothiazol-2-yl-NH- | N-(2-Amino-phenyl)-4-[3-(benzothiazol-2-ylamino)-propenyl]-benzamide | $^1$H NMR (500 MHz, DMSO-d$_6$) δ (ppm): 9.65 (bs, 1H), 8.30 (t, J = 4.9 Hz, 1H), AB system ($δ_A$ = 7.96, $δ_B$ = 7.58, J = 7.8 Hz, 4H), 7.69 (d, J = 7.3 Hz, 1H), 7.42 (d, J = 7.8 Hz, 1H), 7.24 (t, J = 7.8 Hz, 1H), 7.16 (d, J = 6.8 Hz, 1H), 7.04 (t, J = 7.5 Hz, 1H), 6.97 (t, J = 7.6 Hz, 1H), 6.78 (d, J = 7.8 Hz, 1H), 6.71 (d, J = 16.1 Hz, 1H), 6.62–6.51 (m, 2H), 4.89 (bs, 2H), 4.26–4.19 (m, 2H). | 5 |
| XVd | 4-methoxy-6-methyl-pyrimidin-2-yl-NH- | N-(2-Amino-phenyl)-4-[3-(4-methoxy-6-methyl-pyrimidin-2-ylamino)-propenyl]-benzamide | $^1$H NMR (500 MHz, DMSO-d$_6$) δ (ppm) mixture of rotamers, 9.63 (bs, 1H), AB system ($δ_A$ = 7.93, $δ_B$ = 7.53, J = 7.5 Hz, 4H), 7.35–7.05 (m, 2H), 6.96 (t, J = 6.5 Hz, 1H), 6.77 (d, J = 7.9 Hz, 1H), 6.65–6.40 (m, 3H), 5.91 (bs, 1H), 4.15–4.03 (m, 2H), 3.80 (bs,3H), 2.16 (bs, 3H). | 5 |
| XVe | MeS-[1,2,4]triazol-3-yl-NH- | N-(2-Amino-phenyl)-4-[3-(5-methylsulfanyl-1H-[1,2,4]triazol-3-ylamino)-propenyl]-benzamide | $^1$H NMR (500 MHz, DMSO-d$_6$) δ (ppm): 12.16 (bs, 1H), 9.64 (s, 1H), 8.00–7.90 (m, 2H), 7.60–7.50 (m, 2H), 7.20–7.13 (m, 1H), 7.02–6.85 (m, 2H), 6.82–6.75 (m, 1H), 6.67–6.55 (m, 2H), 6.55–6.42 (m, 1H), 4.88 (bs, 2H), 3.93 (bs, 2H), 2.42 (s, 3H). | 5 |

TABLE 4-continued

XV

| Cmpd | Rx- | Name | Characterization | Scheme |
|------|-----|------|------------------|--------|
| XVf | (6-acetylbenzo[1,3]dioxol-5-yl structure) | 4-[3-(6-Acetyl-benzo[1,3]dioxol-5-ylamino)-propenyl]-N-2-amino-phenyl)-benzamide | $^1$H NMR (400 MHz, DMSO-$d_6$) δ (ppm) 9.64 (s, 1H), 9.47 (t, J = 6.0 Hz, 1H), 7.92 (d, J = 8.4 Hz, 2H), 7.54 (d, J = 8.4 Hz, 2H), 7.32 (s, 1H), 7.13 (d, J = 8.0 Hz, 1H), 6.95 (td, J = 8.4, 1.6 Hz, 1H), 6.76 (dd, J = 8.4, 1.6 Hz, 1H), 6.63 (d, J = 16.0 Hz, 1H), 6.58 (td, J = 8.4, 1.6 Hz, 1H), 6.54 (dt, J = 16.0, 5.6 Hz, 1H), 6.46 (s, 1H), 5.97 (s, 2H), 4.88 (s, 2H), 4.07 (t, J = 5.6 Hz, 2H), 2.45 (s, 3H). | 5 |
| XVg | (3,4-dimethoxyphenyl structure) | N-(2-Amino-phenyl)-4-[3-(3,4-dimethoxy-phenylamino)-propenyl]-benzamide | $^1$H NMR (400 MHz, DMSO-$d_6$) δ (ppm) 9.67 (s, 1H), AB system ($δ_A$ = 7.96, $δ_B$ = 7.56, J = 8.2 Hz, 4H), 7.18 (d, J = 6.7 Hz, 1H), 6.99 (td, J = 7.6, 1.6 Hz, 1H), 6.80 (dd, J = 8.0, 1.4 Hz, 1H), ABX system ($δ_A$ = 6.74, $δ_B$ = 6.13, $δ_X$ = 6.37, $J_{AB}$ = 8.5 Hz, $J_{BX}$ = 2.6 Hz, $J_{AX}$ = 0 Hz, 3H), 6.71 (d, J = 16.2 Hz, 1H), 6.62 (td, J = 7.5, 1.4 Hz, 1H), 6.52 (dt, J = 16.0, 5.5 Hz, 1H), 5.59 (t, J = 5.9 Hz, 1H), 4.92 (s, 2H), 3.88 (t, J = 4.9 Hz, 2H), 3.72 (s, 3H), 3.65 (s, 3H). | 7 (Pathway B) |
| XVh | (4-pyridin-3-yl-pyrimidin-2-yl structure) | N-(2-Amino-phenyl)-4-[3-(4-pyridin-3-yl-pyrimidin-2-ylamino)-propenyl]-benzamide | $^1$H NMR (400 MHz, DMSO-$d_6$) δ (ppm) 9.65 (s, 1H), 9.31 (s, 1H), 8.71 (dd, J = 4.8, 1.7 Hz, 1H), 8.53–8.42 (m, 2H), 7.95 (d, J = 8.2 Hz, 2H), 7.67 (t, J = 5.9 Hz, 1H), 7.60–7.52 (m, 3H), 7.30 (d, J = 5.1 Hz, 1H), 7.17 (d, J = 6.7 Hz, 1H), 6.99 (td, J = 7.6, 1.6 Hz, 1H), 6.79 (dd, J = 8.0, 1.4 Hz, 1H), 6.69 (bd, J = 16.0 Hz, 1H), 6.64–6.53 (m, 2H), 4.92 (s, 2H), 4.32–4.20 (m, 2H). | 7 (Pathway B) |

Example 37

N-(2-Amino-phenyl)-4-(3-oxo-3-phenyl-propenyl)-benzamide (XXIVa)

Step 1: 4-(3-Oxo-3-phenyl-propenyl)-benzoic acid (XIIIa)

To a stirred suspension at room temperature of 4-formyl-benzoic acid (2.58 g, 17 mmol) and acetophenone (2.0 ml, 17 mmol) or acetophenone derivatives (1.0–1.1 equiv.) in MeOH (100 ml) was added a solution of NaOH (34 ml, 1N in H$_2$O). After 16 h, the reaction mixture was acidified with conc. HCl (pH=1–2), filtered off, rinsed with H$_2$O and dried to afford the title compound XXIIIa (3.73 g, 14.6 mmol, 86% yield) as a yellow solid.

Step 2: N-(2-Amino-phenyl)-4-(3-oxo-3-phenyl-propenyl)-benzamide (XXIVa)

The title compound XXIVa was obtained from XXIIIa in one step following the same procedure as Example 1, step 2 (Scheme 1). $^1$H NMR (300 MHz, DMSO-$d_6$) δ(ppm): 9.77 (s, 1H); 8.21 (d, J=7.0 Hz, 2H); 8.06 (m, 5H), 7.82 (d, J=15.4 Hz, 1H), 7.71 (t, J=7.3 Hz, 1H), 7.60 (t, J=7.3 Hz, 2H), 7.18 (d, J=7.9 Hz, 1H), 6.99 (t, J=7.0 Hz, 1H), 6.80 (d, J=7.5 Hz, 1H), 6.61 (t, J=7.3 Hz, 1H), 4.95 (bs, 2H).

Examples 38–41

Examples 38 to 41 (compounds XXIVb–XXIVe) were prepared using the same procedure as described for compound XXIVa of Example 37 (Scheme 8).

Example 42

N-(2-Amino-phenyl)-4-[3-(4-morpholin-4-yl-phenyl)-3-oxo-propenyl]-benzamide (XXIVf)

Step 1: t-Butyl (2-{4-[3-(4-morpholin-4-yl-phenyl)-3-oxo-propenyl]-benzoylamino}-phenyl)-carbamate To a stirred solution at room temperature of XI (210 mg, 0.62 mmol), 4'-morpholino acetophenone (227 mg, 1.11 mmol) or acetophenone derivative (1.5–2.0 equiv.) in MeOH (10 ml) was added a solution of NaOH (1.9 ml, 1N in H$_2$O). A precipitate appeared. After 3 days, the reaction mixture was filtered off, rinsed with MeOH, air-dried and dried under vacuum to afford the title compound XXVf (295 mg, 0.56 mmol, 90% yield) as a yellow solid.

Step 2: N-(2-Amino-phenyl)-4-[3-(4-morpholin-4-yl-phenyl)-3-oxo-propenyl]-benzamide (XXIVf)

To a stirred solution at room temperature of XXVf (285 mg, 0.54 mmol) in CH$_2$Cl$_2$ (10 ml) was added trifluoroacetic acid (2 ml, 95% in water). After 17 h, the reaction mixture was concentrated, diluted with AcOEt, successively washed with sat NaHCO$_3$, H$_2$O, sat NH$_4$Cl, H$_2$O and brine, dried over MgSO$_4$, filtered, and concentrated. The crude product was co-precipitated in a mixture of AcOEt/hexane and triturated. After few hours, the suspension was filtered off, rinsed with hexane and dried to afford the title compound XXIVf (210 mg, 0.49 mmol, 91% yield) as a yellow-orange solid. $^1$H NMR (300 MHz, DMSO-$d_6$) δ(ppm): 9.78 (s, 1H), 8.25–7.94 (m, 7H), 7.76 (d, J=15.4 Hz, 1H), 7.22 (d, J=7.5 Hz, 1H), 7.09 (d, J=8.8 Hz, 2H), 7.03 (t, J=7.7 Hz, 1H), 6.83 (s, J=7.5 Hz, 1H), 6.65 (t, J=7.5 Hz, 1H), 4.97 (bs, 2H), 3.88–3.70 (m, 4H), 3.48–3.30 (m, 4H).

TABLE 5

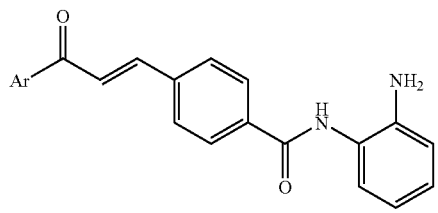

XXIV

| Cmpd | Ar | NAME | Characterization | Scheme |
|---|---|---|---|---|
| XXIVb | 2-nitrophenyl | N-(2-Amino-phenyl)-4-[3-(2-nitro-phenyl)-3-oxo-propenyl]-benzamide | $^1$H NMR (300 MHz, DMSO-$d_6$) δ (ppm) 9.73 (s, 1H), 8.22 (d, J = 7.6 Hz, 1H), 8.03–7.76 (m, 7H), 7.51–7.39 (m, 2H), 7.16 (d, J = 7.6 Hz, 1H), 6.97 (t, J = 7.6 Hz, 1H), 6.78 (d, J = 7.6 Hz, 1H), 6.59 (t, J = 7.3 Hz, 1H), 4.92 (bs, 2H). | 8 |
| XXIVc | 4-methoxyphenyl | N-(2-Amino-phenyl)-4-[3-(4-methoxy-phenyl)-3-oxo-propenyl]-benzamide | $^1$H NMR (300 MHz, DMSO-$d_6$) δ (ppm) 9.75 (bs, 1H), 8.21 (d, J = 8.8 Hz, 2H), 8.11–8.01 (m, 5H), 7.77 (d, J = 15.4 Hz, 1H), 7.18 (d, J = 7.3 Hz, 1H), 7.11 (d, J = 8.8 Hz, 2H), 6.99 (dd, J = 7.7, 7.7 Hz, 1H), 6.79 (d, J =7.3 Hz, 1H), 6.61 (dd, J = 7.3, 7.3 Hz, 1H), 4.94 (bs, 2H), 3.88 (s, 3H). | 8 |
| XXIVd | 3-methoxyphenyl | N-(2-Amino-phenyl)-4-[3-(3-methoxy-phenyl)-3-oxo-propenyl]-benzamide | $^1$H NMR (300 MHz, DMSO-$d_6$) δ (ppm) 9.75 (bs, 1H), 8.08–8.03 (m, 5H), 7.83–7.78 (m, 2H), 7.65 (bs, 1H), 7.51 (dd, J = 7.7, 7.7 Hz, 1H), 7.27 (dd, J = 8.4, 2.3 Hz, 1H), 7.17 (d, J = 8.1 Hz, 1H), 6.98 (dd, J = 7.3, 7.3 Hz, 1H), 6.79 (d, J = 7.3 Hz, 1H), 6.60 (dd, J = 7.3, 7.3 Hz, 1H), 4.93(bs, 2H), 3.87 (s, 3H). | 8 |
| XXIVe | 2-methoxyphenyl | N-(2-Amino-phenyl)-4-[3-(2-methoxy-phenyl)-3-oxo-propenyl]-benzamide | $^1$H NMR (300 MHz, DMSO-$d_6$) δ (ppm) 9.73 (bs, 1H), 8.03 (d, J = 8.1 Hz, 2H), 7.88 (d, J = 8.1 Hz, 2H), 7.61–7.50 (m, 4H), 7.22 (d, J = 8.1 Hz, 1H), 7.17 (d, J = 8.1 Hz, 1H), 7.08 (dd, J = 7.3, 7.3 Hz, 1H), 6.98 (dd, J = 7.7, 7.7 Hz, 1H), 6.78 (d, J = 7.3 Hz, 1H), 6.60 (dd, J = 7.7,7.7 Hz, 1H), 4.93 (bs, 2H), 3.89 (s, 3H). | 8 |

Example 43

N-(2-Amino-phenyl)-4-(3-oxo-3-phenyl-propyl)-benzamide (XXVIIa)

Step 1: 4-(3-Oxo-3-phenyl-propyl)-benzoic acid (XXVIa)

To a stirred solution at room temperature of chalcone XXIIIa (1.29 g, 5.13 mmol) in DMF (20 ml) was added phenylsulfonylhydrazine (1.76 g, 10.26 mmol). The reaction mixture was stirred at 10° C. for 15 h, cooled and concentrated. The remained oily residue was partitioned between a saturated aqueous solution of NH$_4$Cl and AcOEt. After separation, the organic layer was dried, partially evaporated and filtered. The filtrate was purified by flash chromatography on silica gel (AcOEt/hexane:50/50□75/25) to form a material which after a second column purification (MeOH/CH$_2$Cl$_2$:5/95) afford the title compound XXVIa (400 mg, 1.59 mmol, 31% yield).

Step 2: N-(2-Amino-phenyl)-4-(3-oxo-3-phenyl-propyl)-benzamide (XXVIIa)

The title compound XXVIIa was obtained from XXVIa in one step following the same procedure as Example 1, step 2 (Scheme 1). $^1$H NMR (300 MHz, DMSO-$d_6$) δ(ppm): 9.59 (s, 1H); 8.00 (d, J=7.5 Hz, 2H); 7.90 (d, J=7.9 Hz, 2H); 7.64 (t, J=7.5 Hz, 2H), 7.43 (d, J=7.9 Hz, 2H), 7.16 (d, J=7.5 Hz, 1H), 6.97 (t, J=7.0 Hz, 1H), 6.78 (d, J=7.0 Hz, 1H), 6.59 (t, J=7.5 Hz, 1H), 4.88 (bs, 2H), 3.44 (t, J=7.3 Hz, 2H), 3.03 (t, J=7.3 Hz, 2H).

Example 44

N-(2-Amino-phenyl)-4-(3-phenyl-propyl)-benzamide (XXIXa)

Step 1: 4-(3-Phenyl-propyl)-benzoic acid (XXVIIIa)

A stirred solution at room temperature of XXIIIa (1.34 g, 5.31 mmol) in 25 ml DMA was hydrogenated over 10% Pd/C (600 mg, Degussa type) at 1 atm for 3 h. After removal of the catalyst by filtration through celite pad, the solution was concentrated and the residue was treated with water. After precipitation, the suspension was filtered off, rinsed with H$_2$O, and dried to afford the title compound XXVIIIa (1.13 g, 4.72 mmol, 89% yield).

Step 2: N-(2-Amino-phenyl)-4-(3-phenyl-propyl)-benzamide (XXIXa)

The title compound XXIXa was obtained from XXVIIIa in one step following the same procedure as Example 1, step 2 (Scheme 1). $^1$H NMR (300 MHz, DMSO-$d_6$) δ(ppm): 9.60 (s, 1H); 7.91 (d, J=7.9 Hz, 2H); 7.34 (d, J=8.4 Hz, 2H), 7.28 (d, J=7.5 Hz, 2H), 7.23–7.15 (m, 4H), 6.97 (t, J=7.0 Hz, 1H), 6.78 (d, J=7.5 Hz, 1H), 6.59 (t, J=7.3 Hz, 1H), 4.88 (bs, 2H), 2.71–2.59 (m, 4H), 1.92 (m, 2H).

Example 45

N-(2-Amino-phenyl)-4-[3-(1,3-dihydro-isoindol-2-yl)-propenyl]-benzamide (XXXa)

Step 1: Methyl 4-trimethylsilanylethynyl-benzoate (XXXI)

A stirred solution at room temperature of methyl 4-bromobenzoate (8.84 g, 41.11 mmol), Pd(PPh$_3$)$_2$Cl$_2$ (840 mg, 1.20 mmol) and CuI (455 mg, 2.39 mmol) in anhydrous THF (200 ml) was saturated with nitrogen for 15 min. Then, the solution under nitrogen was cooled down at 0° C., and trimethylsilylacetylene (7.2 ml, 50.91 mmol) and triethylamine (22 ml, 157.8 mmol) were added successively. The reaction mixture was allowed to warm up at room temperature. After 2 h, Pd(PPh$_3$)$_2$Cl$_2$ (100 mg) and CuI (80 mg) and trimethylsilylacetylene (0.5 ml) were added again, and the reaction mixture was stirred overnight. Then, the reaction mixture was diluted with AcOEt and successively washed with a saturated aqueous solution of NH$_4$Cl and brine, dried over MgSO$_4$, filtered and concentrated. The crude residue was then purified by flash chromatography on silica gel (AcOEt/hexane:5/95☐10/90) to afford the title compound XXXI (9.05 g, 38.95 mmol, 94% yield) as a yellow sticky solid. $^1$H NMR: (400 MHz, CDCl$_3$) δ (ppm): AB system ($\delta_A$=7.67, $\delta_B$=7.22, $J_{AB}$=8.5 Hz, 4H), 3.63 (s, 3H), 0.00 (s, 9H).

Step 2: Methyl 4-ethynyl-benzoate (XXXII)

To a stirred solution at 0° C. under nitrogen of XXXI (9.05 g, 38.95 mmol) in MeOH (280 ml) was added potassium carbonate (1.62 g, 11.72 mmol). After 3 h, the reaction mixture was concentrated and directly purified by flash chromatography on silica gel (CH$_2$Cl$_2$:100) to afford the title compound XXXII (6.16 g, 38.46 mmol, 98% yield) as a pale yellow solid. $^1$H NMR: (400 MHz, CDCl$_3$) δ (ppm): AB system ($\delta_A$=7.98, $\delta_B$=7.54, $J_{AB}$=8.6 Hz, 4H), 3.93 (s, 3H), 3.24 (s, 1H).

Step 3: β-(4-methoxycarbonyl)-styrylboronic acid (XXXIII)

To a stirred solution at room temperature under nitrogen of XXXII (6.16 g, 38.46 mmol) in anhydrous THF (15 ml) was added catecholborane (4.52 ml, 42.80 mmol). The reaction mixture was heated to 70° C. for 4 h, and catecholborane (2 ml) was added again. After 1.5 h, the reaction mixture was allowed to cool down at room temperature, and an aqueous solution of 2N HCl (50 ml) was added and stirred overnight. Then, it was concentrated on the Rotavap, filtered off and the cake was triturated in toluene. After filtration, the intermediate solid was dissolved in THF (50 ml) and an aqueous solution of 2N HCl (150 ml) was added. The resulting suspension was warmed to 40° C. for overnight, filtered off, rinsed with water, air-dried and dried under vacuum to afford the title compound XXXIII (3.10 g, 15.05 mmol, 39% yield) as an off-white fluffy solid. $^1$H NMR: (400 MHz, DMSO-d$_6$) δ (ppm): AB system ($\delta_A$=7.96, $\delta_B$=7.63, $J_{AB}$=8.4 Hz, 4H), 7.94 (s, 2H), 7.32 (d, J=18.2 Hz, 1H), 6.30 (d, J=18.2 Hz, 1H), 3.88 (s, 3H).

Step 4: Methyl 4-[3-(1,3-Dihydro-isoindol-2-yl)-propenyl]-benzoate (XXXIVa)

To a stirred solution pre-heated at 90° C. for 15 min under nitrogen of isoindoline (116 mg, 0.97 mmol) and paraformaldehyde (32 mg, 1.07 mmol) in anhydrous 1,4-dioxane (10 ml) was added XXXIII (245 mg, 1.17 mmol). After stirring at 90° C. for overnight, the reaction mixture was allowed to cool down to room temperature, an aqueous solution of 2N HCl (30 ml) was added and shacked for 30 min. Then, the aqueous mixture was extracted with Et$_2$O, basified with 2N NaOH (50 ml), and extracted with CH$_2$Cl$_2$. The combined dichoromethane layer was dried over MgSO$_4$, filtered and concentrated. The crude residue was then purified by flash chromatography on silica gel (MeOH/CH$_2$Cl$_2$:5/95) to afford the title compound XXXIVa (135 mg, 0.46 mmol, 48% yield) as an off-white solid. $^1$H NMR: (400 MHz, DMSO-d$_6$) δ (ppm): AB system ($\delta_A$=7.93, $\delta_B$=7.64, $J_{AB}$=8.4 Hz, 4H), 7.29–7.17 (m,4H), 6.75 (d, J=15.8 Hz, 1H), 6.62 (dt, J=16.0, 6.3 Hz, 1H), 3.94 (s, 4H), 3.88 (s, 3H), 3.55 (dd, J=6.1, 1.0 Hz, 2H).

Step 5: N-(2-Amino-phenyl)-4-[3-(1,3-dihydro-isoindol-2-yl)-propenyl]-benzamide (XXXa)

The title compound XXXa was obtained from XXXIVa in two steps following the same procedure as Example 11, steps 5 and 6 (Scheme 3). $^1$H NMR (400 MHz, DMSO-d$_6$) δ(ppm): 9.67 (s, 1H), AB system ($\delta_A$=7.98, $\delta_B$=7.63, $J_{AB}$=8.3 Hz, 4H), 7.30–7.15 (m, 5H), 7.00 (td, J=7.6, 1.5 Hz, 1H), 6.81 (dd, J=8.0, 1.4 Hz, 1H), 6.75 (d, J=15.8 Hz, 1H), 6.66–6.56 (m, 2H), 4.93 (s, 2H), 3.95 (s, 4H), 3.56 (dd, J=6.2, 0.9 Hz, 2H).

Examples 46–49

Examples 46 to 49 (compounds XXXb–XXXe) were prepared using the same procedure as described for compound XXXa of Example 45 (Scheme 11).

TABLE 6

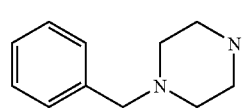

| Cmpd | RX- | NAME | Characterization | Scheme |
|---|---|---|---|---|
| XXXb | ![structure] | N-(2-Amino-phenyl)-4-[3-(4-benzyl-piperazin-1-yl)-propenyl]-benzamide | $^1$H NMR (400 MHz, CDCl$_3$) δ (ppm): 7.84 (d, J = 8.0 Hz, 3H), 7.46 (d, J = 8.0 Hz, 2H), 7.35–7.22 (m, 6H), 7.09 (td, J = 7.6, 1.6 Hz, 1H), 6.88–6.81 (m, 2H), 6.58 (d, J = 15.6 Hz, 1H), 6.41 (dt, J = 15.6, 6.8 Hz, 1H), 3.88 (bs, 2H), 3.57 (s, 2H), 3.24 (d, J = 6.8 Hz, 2H), 2.59 (bs, 8H). | 11 |

TABLE 6-continued

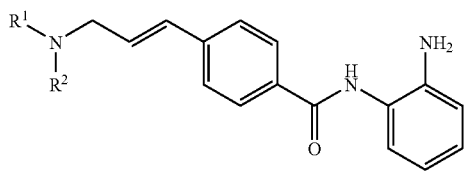

XXX

| Cmpd | RX- | NAME | Characterization | Scheme |
|---|---|---|---|---|
| XXXc | | N-(2-Amino-phenyl)-4-[3-(4-pyridin-2-yl-piperazin-1-yl)-propenyl]-benzamide | $^1$H NMR (400 MHz, DMSO-$d_6$) δ (ppm) 9.63 (s, 1H), 8.09–8.08 (m, 1H), 7.93 (d, J = 8.0 Hz, 2H), 8.0 (d, J = 2.5 Hz, 1H), 7.51 (t, J = 7.3 Hz, 1H), 7.14 (d, J = 7.6, 1H), 6.95 (td, J = 7.6, 1.2 Hz, 1H), 6.81 (d, J = 8.6, 1H), 6.76 (dd, J = 8.0, 1.4 Hz, 1H), 6.69–6.60 (m, 2H), 6.58 (td, J = 7.6, 1.3 Hz, 1H), 6.49 (dt, J = 16.0, 6.5 Hz, 1H), 4.89 (s, 2H), 3.48–3.15 (m, 6H), 2.53–2.45 (m, 4H). | 11 |
| XXXd | | N-(2-Amino-phenyl)-4-[3-(benzyl-methyl-amino)-propenyl]-benzamide | $^1$H NMR (400 MHz, DMSO-$d_6$) δ (ppm) 9.66 (s, 1H), 7.96 (bd, J = 8.2 Hz, 2H), 7.60 (bd, J = 8.2 Hz, 2H), 7.34 (s, 2H), 7.36 (d, J = 1.2 Hz, 2H), 7.30–7.25 (m, 1H), 7.18 (d, J = 7.0 Hz 1H), 6.99 (td, J = 7.6, 1.5 Hz, 1H), 6.76 (dd, J = 7.9, 1.5 Hz, 1H), 6.68 (d, J = 15.8, 1H), 6.62 (td, J = 7.5,1.4 Hz, 1H), 6.54 (dt, J = 16.2, 6.5 Hz, 1H), 4.92 (bs, 2H), 3.57 (s, 2H), 3.22 (d, J = 6.3 Hz, 2H), 2.20 (s, 3H). | 11 |
| XXXe | | N-(2-Amino-phenyl)-4-[3-(indan-2-ylamino)-propenyl]-benzamide | $^1$H NMR (400 MHz, DMSO-$d_6$) δ (ppm) 9.71 (s, 1H), 8.02 (d, J = 8.2 Hz, 2H), 7.64 (d, J = 8.4 Hz, 2H), 7.32–7.22 (m, 4H), 7.18 (d, J = 7.6 Hz, 1H), 7.00 (t, J = 8.1 Hz, 1H), 6.87 (d, J = 16.0 Hz, 1H), 6.80 (d, J = 9.2 Hz, 1H), 6.63 (t, J = 7.7 Hz, 1H), 6.50 (dt, J = 15.8, 6.7 Hz, 1H), 4.93(bs, 2H), 4.13 (m, 1H), 3.87 (d, J = 7.6 Hz, 2H), 3.37–3.32 (m, 2H), 3.14 (d, J = 7.6 Hz, 2H). | 11 |

Example 50

Inhibition of Histone Deacetylase Enzymatic Activity

1. Human HDAC-1: Assay 1

HDAC inhibitors were screened against a cloned recombinant human HDAC-1 enzyme expressed and purified from a Baculovirus insect cell expression system. For deacetylase assays, 20,000 cpm of the [$^3$H]-metabolically labeled acetylated histone substrate (M. Yoshida et al., *J. Biol. Chem.* 265(28): 17174–17179 (1990)) was incubated with 30 μg of the cloned recombinant hHDAC-1 for 10 minutes at 37° C. The reaction was stopped by adding acetic acid (0.04 M, final concentration) and HCl (250 mM, final concentration). The mixture was extracted with ethyl acetate and the released [$^3$H]-acetic acid was quantified by scintillation counting. For inhibition studies, the enzyme was preincubated with compounds at 4° C. for 30 minutes prior to initiation of the enzymatic assay. IC$_{50}$ values for HDAC enzyme inhibitors were determined by performing dose response curves with individual compounds and determining the concentration of inhibitor producing fifty percent of the maximal inhibition. IC$_{50}$ values for representative compounds assayed using this procedure are presented in the third column of Tables 7–10 (excepting bracketed data).

2. Human HDAC-1: Assay 2

In the alternative, the following protocol was used to assay the compounds of the invention. In the assay, the buffer used was 25 mM HEPES, pH 8.0, 137 mM NaCl, 2.7 mM KCl, 1 mM MgCl$_2$ and the substrate was Boc-Lys(Ac)-AMC in a 50 mM stock solution in DMSO. The enzyme stock solution was 4.08 μg/mL in buffer.

The compounds were pre-incubated (2 μl in DMSO diluted to 13 μl in buffer for transfer to assay plate) with enzyme (20 μl of 4.08 μg/ml) for 10 minutes at room temperature (35 μl pre-incubation volume). The mixture was pre-incubated for 5 minutes at room temperature. The reaction was started by bringing the temperature to 37° C. and adding 16 μl substrate. Total reaction volume was 50 μl. The reaction was stopped after 20 minutes by addition of 50 μl developer, prepared as directed by Biomol (Fluor-de-Lys developer, Cat. # KI-105). A plate was incubated in the dark for 10 minutes at room temperature before reading ($\lambda_{EX}$=360 nm, $\lambda_{Ex}$=470 nm, Cutoff filter at 435 nm).

IC$_{50}$ values for representative compounds assayed using this procedure are presented in the third column of Table 9 (bracketed [ ] data).

3. MTT Assay

HCT116 cells (2000/well) were plated into 96-well tissue culture plates one day before compound treatment. Compounds at various concentrations were added to the cells. The cells were incubated for 72 hours at 37° C. in 5% CO$_2$ incubator. MTT (3-[4,5-dimethylthiazol-2-yl]-2,5 diphenyl tetrazolium bromide, Sigma) was added at a final concentration of 0.5 mg/ml and incubated with the cells for 4 hours before one volume of solubilization buffer (50% N,N-dimethylformamide, 20% SDS, pH 4.7) was added onto the cultured cells. After overnight incubation, solubilized dye was quantified by colorimetric reading at 570 nM using a reference at 630 nM using an MR700 plate reader (Dynatech Laboratories Inc.). OD values were converted to cell numbers according to a standard growth curve of the relevant cell line. The concentration which reduces cell numbers to 50% of that of solvent treated cells is determined as MTT IC$_{50}$. IC$_{50}$ values for representative compounds are presented in the fourth column of Tables 7–10.

4. Histone H4 Acetylation in Whole Cells by Immunoblots

T24 human bladder cancer cells growing in culture were incubated with HDAC inhibitors for 16 h. Histones were extracted from the cells after the culture period as described by M. Yoshida et al. (*J. Biol. Chem.* 265(28): 17174–17179 (1990)). 20 g of total histone protein was loaded onto SDS/PAGE and transferred to nitrocellulose membranes. Membranes were probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection was performed using Kodak films (Eastman Kodak). Acetylated H-4 signal was quantified by densitometry. Representative data are presented in the fifth column of Table 7–10. Data are presented as the concentration effective for reducing the acetylated H-4 signal by 50% (EC$_{50}$).

TABLE 7

| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Ia | 3,4-dichlorophenyl chalcone derivative | 5 | 1 | na |
| Ib | 3-pyridyl chalcone derivative | 2 | 0.9 | 5 |
| Ic | 2,6-dichlorophenyl chalcone derivative | 3 | 0.4 | 9999 |
| Id | 3,4,5-trimethoxyphenyl chalcone derivative | 3 | 0.6 | 3 |

TABLE 7-continued

[Structure: Ar-CH=CH-C(=O)-C6H4-C(=O)NH-C6H4-NH2]

| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Ie | 4-Cl-C6H4-CH=CH-C(=O)-C6H4-C(=O)NH-C6H4-NH2 | 6 | 9 | na |
| If | 2,4,6-(MeO)3-C6H2-CH=CH-C(=O)-C6H4-C(=O)NH-C6H4-NH2 | 4 | 5 | na |
| Ig | 3-cyclopropoxy-4-(OCHF2)-C6H3-CH=CH-C(=O)-C6H4-C(=O)NH-C6H4-NH2 | 3 | 0.7 | 9999 |
| Ih | 4-CF3-C6H4-CH=CH-C(=O)-C6H4-C(=O)NH-C6H4-NH2 | 5 | 1 | 5 |
| Ii | 2,5-F2-C6H3-CH=CH-C(=O)-C6H4-C(=O)NH-C6H4-NH2 | 3 | 1 | 3 |

TABLE 7-continued
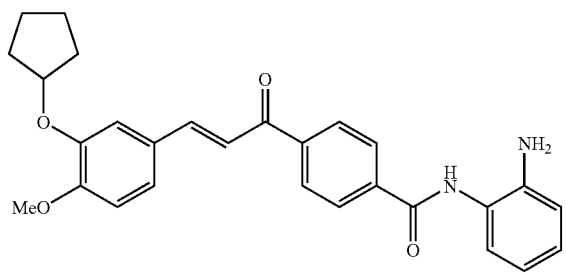
| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Ij | 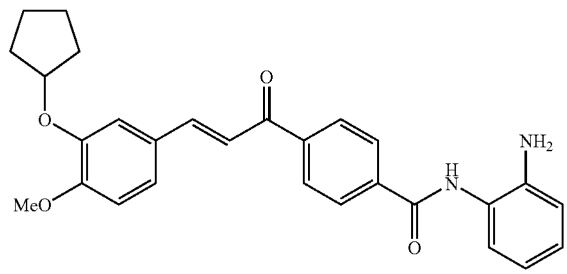 | 4 | 0.7 | 5 |
(na = non available, 9999 = >25 mM)
TABLE 8
| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Va | 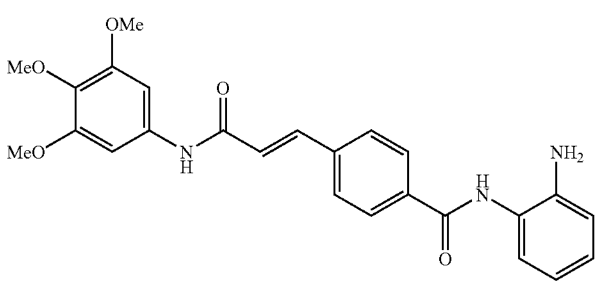 | 5 | 3 | na |
| Vb | 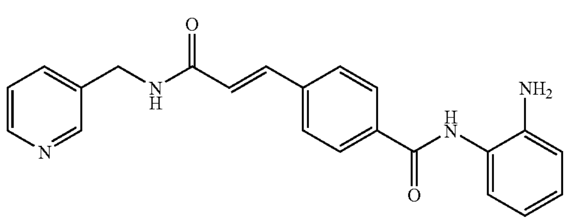 | 3 | 0.07 | 1 |

TABLE 8-continued

| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Vc | (3,4,5-trimethoxybenzyl amide derivative) | 3 | 0.9 | 2 |
| Vd | (phenoxyethyl amide derivative) | 1 | 0.4 | 1 |
| Ve | (morpholine amide derivative) | 20 | 6 | na |
| Vf | (pyridin-3-ylethyl amide derivative) | 5 | 0.3 | 1 |
| Vg | (pyridin-3-ylmethyl ester derivative) | 10 | 5 | na |

TABLE 8-continued
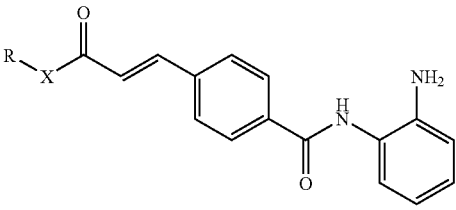
| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| Vh | 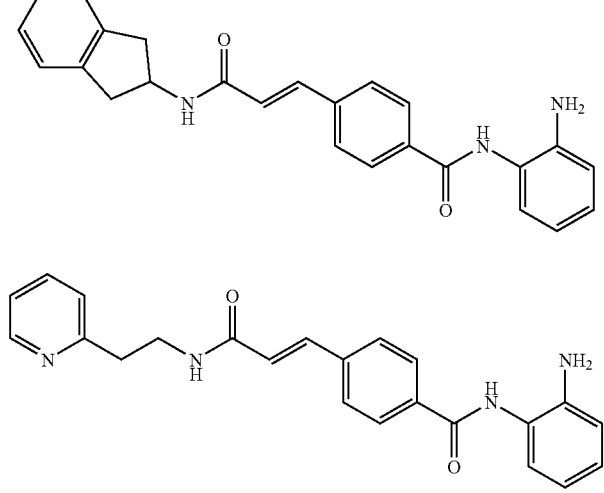 | 3 | 1 | 10 |
| Vi | 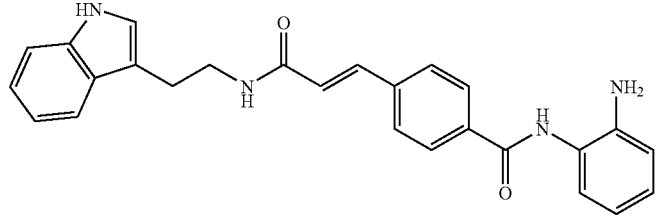 | 4 | 1 | 3 |
| Vj | 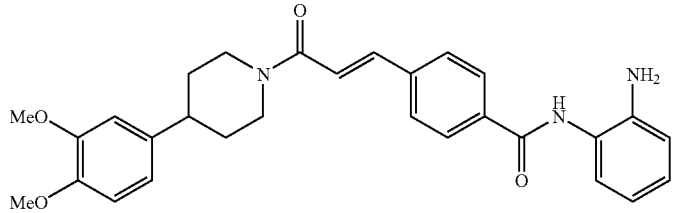 | 1 | 0.3 | 1 |
| Vk | 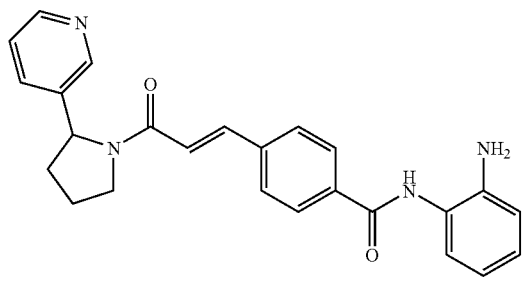 | 13 | 2 | na |
| Vl | 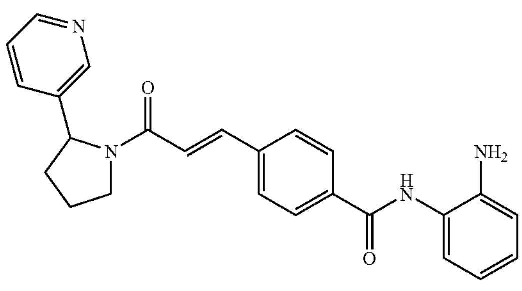 | 12 | 4 | na |

TABLE 8-continued

| Cmpd | Structure | Human HDAC-1 IC$_{50}$ (µM) | MTT(HCT116) IC$_{50}$ (µM) | H4 Ac (T24) EC$_{50}$ (µM) |
|---|---|---|---|---|
| Vm | 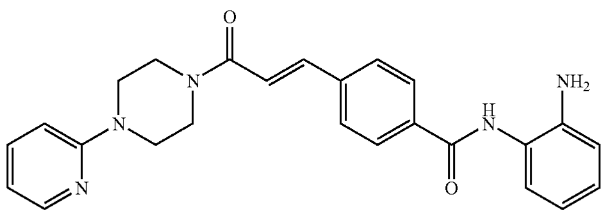 | 11 | 6 | na |
| Vn | 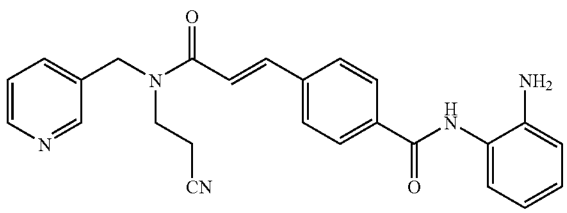 | 7 | 3 | na |
| Vo | 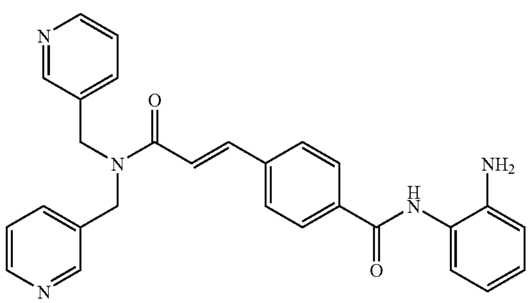 | 15 | 4 | na |
| V9 | 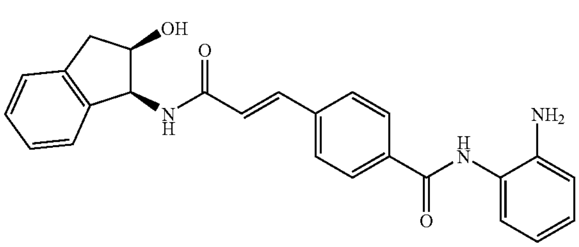 | 13 | 2 | na |

(na = non available, 9999 = >25 mM)

TABLE 9
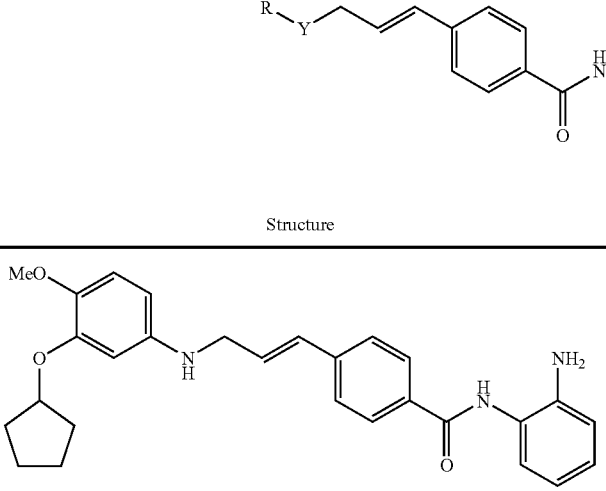
| Cmpd | Structure | Human HDAC-1 IC$_{50}$ (μM) | MTT(HCT116) IC$_{50}$ (μM) | H4 Ac (T24) EC$_{50}$ (μM) |
| --- | --- | --- | --- | --- |
| XVa | 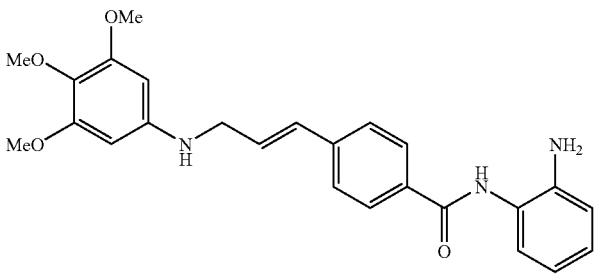 | 2 | 1 | 1 |
| XVb | 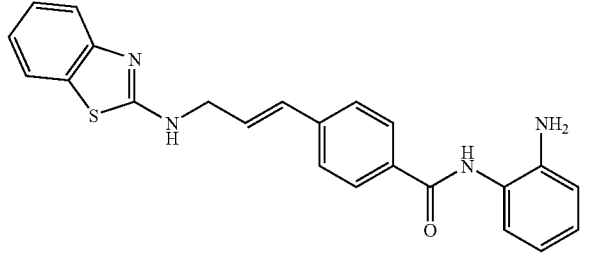 | 4 | 0.1 | 3 |
| XVc | 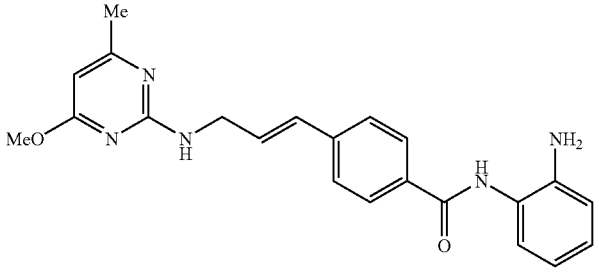 | 0.8 | 1 | <1 |
| XVd | 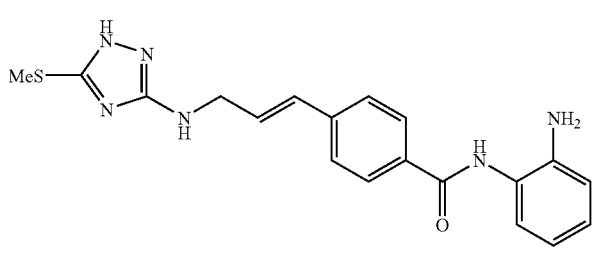 | 4 | 0.3 | 3 |
| XVe | 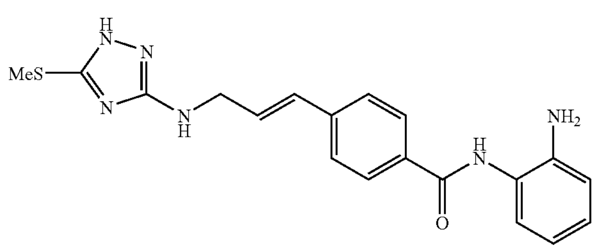 | 2 | 0.5 | 1 |

TABLE 9-continued

| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| XVf | 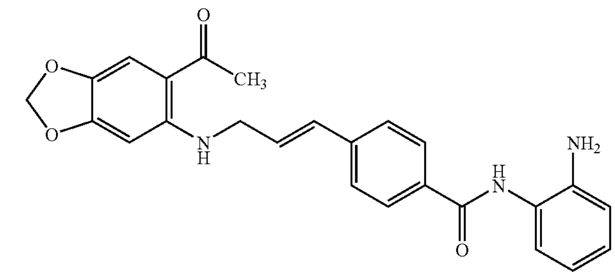 | 3 | 1 | 2 |
| XVg | 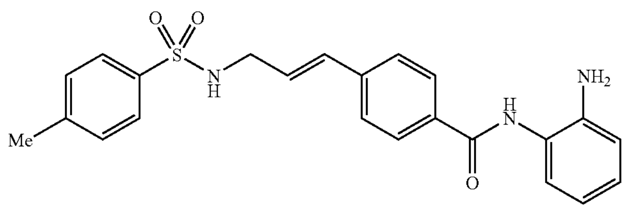 | 12 | 5 | na |
| XXIIh | 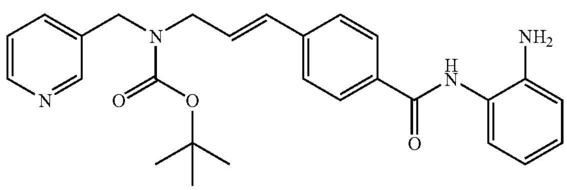 | 3 | 3 | na |
| XVh | 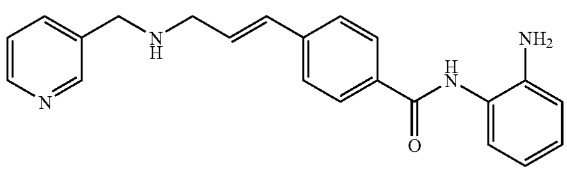 | 4 | 0.7 | 2 |
| XVi | 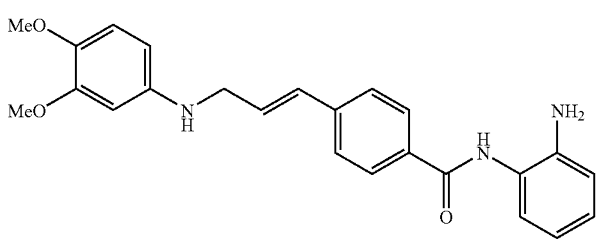 | 1 | 1 | 4 |
| XVj | 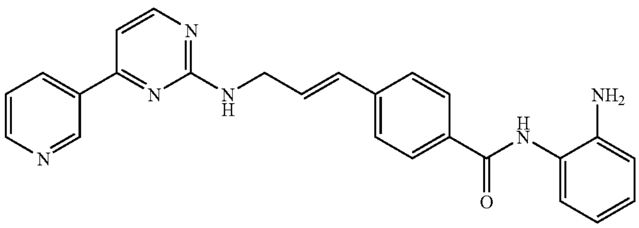 | 2 | 0.2 | <1 |

TABLE 9-continued

| Cmpd | Structure | Human HDAC-1 IC$_{50}$ (μM) | MTT(HCT116) IC$_{50}$ (μM) | H4 Ac (T24) EC$_{50}$ (μM) |
|---|---|---|---|---|
| XXXa | 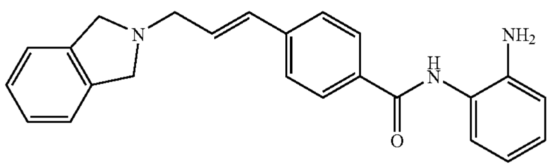 | [0.26] | 1 | 4 |
| XXXb | 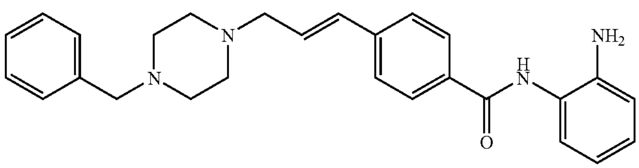 | 4 | 1 | 2 |
| XXXc | 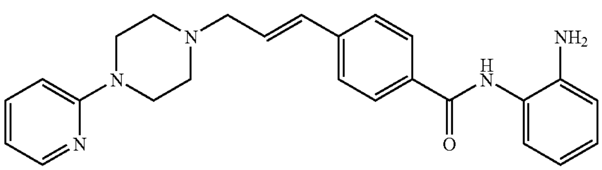 | [0.82] | 0.5 | 2 |
| XXXd | 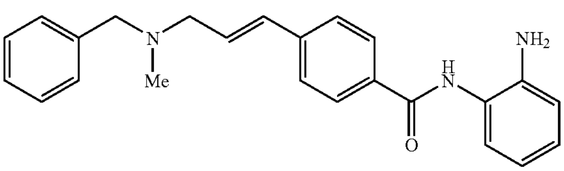 | [0.17] | 2 | na |
| XXXe | 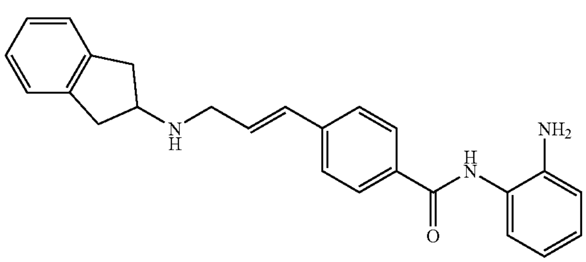 | [0.79] | 2 | na |

(na = non available, 9999 = >25 mM)

TABLE 10

| Cmpd | Structure | Human HDAC-1 IC$_{50}$ (µM) | MTT(HCT116) IC$_{50}$ (µM) | H4 Ac (T24) EC$_{50}$ (µM) |
| --- | --- | --- | --- | --- |
| XXIVa | 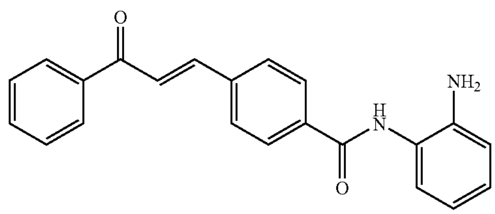 | 4 | 0.4 | 3 |
| XXIVb | 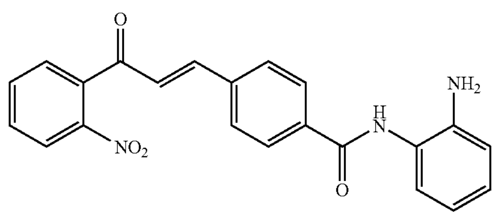 | 8 | 0.1 | 3 |
| XXIVc | 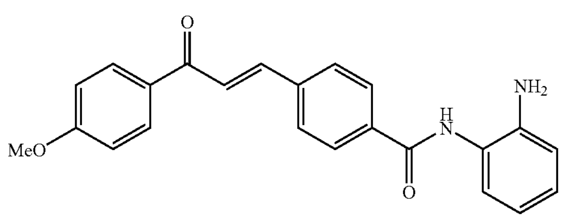 | 13 | 0.6 | 5 |
| XXIVd | 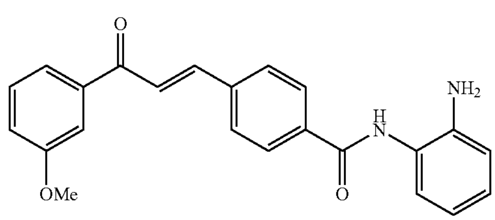 | 4 | 0.3 | <5 |
| XXIVe | 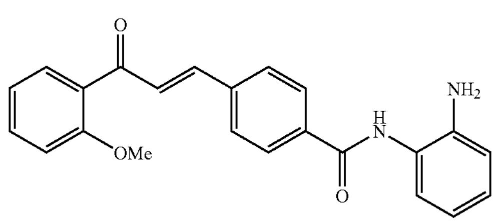 | 3 | 0.8 | 5 |
| XXIVf | 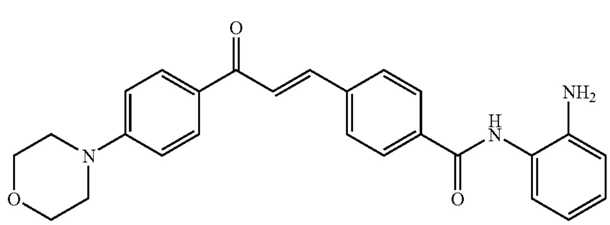 | 10 | 0.3 | 3 |

TABLE 10-continued

| Cmpd | Structure | Human HDAC-1 IC$_{50}$ (µM) | MTT(HCT116) IC$_{50}$ (µM) | H4 Ac (T24) EC$_{50}$ (µM) |
|---|---|---|---|---|
| XXVIIa | 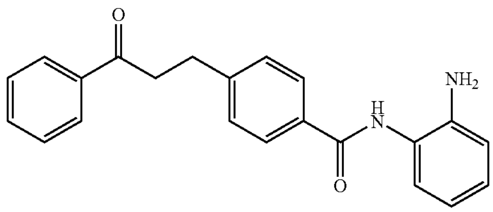 | 2 | 0.6 | 2 |
| XXIXa | 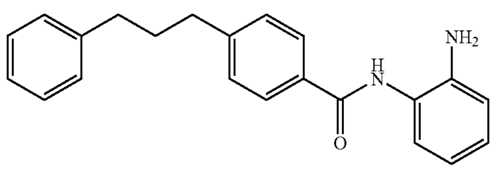 | 2 | 0.6 | na |

(na = non available, 9999 = >25 mM)

Example 51

Antineoplastic Effects of Histone Deacetylase Inhibitors on Human Tumor Xenografts In Vivo Eight to ten week old female CD1 nude mice (Taconic Labs, Great Barrington, N.Y.) were injected subcutaneously in the flank area with 2×10$^6$ preconditioned HCT116 human colorectal carcinoma cells. Preconditioning of these cells was done by a minimum of three consecutive tumor transplantations in the same strain of nude mice. Subsequently, tumor fragments of approximately 30 mgs were excised and implanted subcutaneously in mice, in the left flank area, under Forene anesthesia (Abbott Labs, Geneva, Switzerland). When the tumors reached a mean volume of 100 mm$^3$, the mice were treated intravenously, subcutaneously, or intraperitoneally by daily injection, with a solution of the histone deacetylase inhibitor in an appropriate vehicle, such as PBS, DMSO/water, or Tween 80/water, at a starting dose of 10 mg/kg. The optimal dose of the HDAC inhibitor was established by dose response experiments according to standard protocols. Tumor volume was calculated every second day post infusion according to standard methods (e.g., Meyer et al., *Int. J. Cancer* 43: 851–856 (1989)). Treatment with the HDAC inhibitors according to the invention caused a significant reduction in tumor weight and volume relative to controls treated with vehicle only (i.e., no HDAC inhibitor); a subset of these compounds showed toxicity. The results for compound XVj as an example are displayed in FIG. 1.

We claim:
1. A compound of formula:

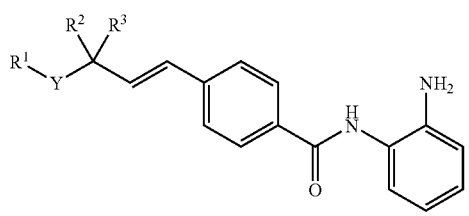

or a pharmaceutically acceptable salt thereof, wherein
Y is —N(R$^4$)—, —O—, —S—, —N(R$^4$)SO$_2$—, —SO$_2$—N(R$^4$)—, —SO$_2$—, —N(R$^4$)—C(O)—, —C(O)—N(R$^4$)—, —NHC(O)NH—, —N(R$^4$)C(O)O—, —OC(O)N(R$^4$)—, or a covalent bond, and
R$^1$, R$^2$, and R$^3$ independently are —H or R$^a$—C$_0$-C$_6$-hydrocarbyl wherein R$^a$ is —H or R$^a$ is aryl or heteroaryl, each of which is optionally substituted with from 1 to 3 substituents,
R$^4$ is —H, —C(O)—R$^b$, —C(O)O—R$^b$, —C(O)NH—R$^b$, or R$^c$–C$_0$-C$_6$-hydrocarbyl wherein
R$^b$ is —H or —C$_1$-C$_6$-hydrocarbyl, and
R$^c$ is —H, or aryl or heteroaryl each of which is optionally substituted with from 1 to 3 substituents.

2. The compound according to claim 1 wherein R$^2$ and R$^3$ are both —H.

3. The compound according to claim 1 wherein Y is —NH—, —SO$_2$—NH—, or —N(R$^4$)— wherein R$^4$ is —C(O)O—C$_1$-C$_6$-hydrocarbyl.

4. The compound according to claim 1 wherein $R^1$ is aryl, benzothiazolyl, pyrimidinyl, triazolyl, benzodioxolenyl, or pyridinyl, each of which is optionally substituted with from 1 to 3 substituents.

5. The compound according to claim 4 wherein $R^1$ is substituted with from 1–3 substituents independently selected from $C_1$–$C_6$-hydrocarbyl, $C_1$–$C_6$-hydrocarbyloxy, halo, methylthio, and acetyl.

6. The compound according to claim 1 wherein $R^1$—Y is selected from:

* * * * *